(12) United States Patent
Rudayni et al.

(10) Patent No.: US 12,257,315 B1
(45) Date of Patent: *Mar. 25, 2025

(54) CANCER TREATMENT METHOD WITH NANOCOMPOSITE

(71) Applicant: IMAM MOHAMMAD IBN SAUD ISLAMIC UNIVERSITY, Riyadh (SA)

(72) Inventors: Hassan A. Rudayni, Riyadh (SA); Ahmed Aly Allam, Riyadh (SA); Aya FadlAllah Abdelmonem Mohamed, Beni Suef (EG); Mostafa R. Abukhadra, Beni Suef (EG); Nohan Nasser Abdelfattah Ahmed, Beni Suef (EG)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/950,997

(22) Filed: Nov. 18, 2024

Related U.S. Application Data

(63) Continuation of application No. 18/778,340, filed on Jul. 19, 2024, now Pat. No. 12,171,841.

(51) Int. Cl.
A61K 47/69 (2017.01)
A61K 9/00 (2006.01)
(Continued)

(52) U.S. Cl.
CPC ........ *A61K 47/6923* (2017.08); *A61K 9/0092* (2013.01); *A61K 33/243* (2019.01);
(Continued)

(58) Field of Classification Search
CPC .. A61K 47/6923; A61K 33/213; A61K 47/02; B82Y 5/00
See application file for complete search history.

(56) References Cited

U.S. PATENT DOCUMENTS

| 5,399,363 A | 3/1995 | Liversidge et al. |
| 11,684,581 B2 | 6/2023 | Kang et al. |
| (Continued) | | |

FOREIGN PATENT DOCUMENTS

WO   WO 2019/108049 A2   6/2019

OTHER PUBLICATIONS

Chandrababu et al, Cisplatin-Functionalized Silica Nanoparticles for Cancer Treatment, Cancer Nano, 4: 127-136. (Year: 2013).*

(Continued)

*Primary Examiner* — Carlos A Azpuru
(74) *Attorney, Agent, or Firm* — Oblon, McClelland, Maier & Neustadt, L.L.P.

(57) ABSTRACT

A method of cytotoxically treating cancer with aluminum silicate nanorods (SNRs) including aluminum, iron, magnesium, oxygen, potassium, and oxygen comprises contacting the SNRs at a concentration of 0.5 to 2 µg/mL with a cancerous sample. The aluminum silicate nanorods have a longest dimension of 100 nanometers (nm) to 5500 nm and a diameter of 20 nm to 250 nm. The SNRs are porous with a pore size of 1 nm to 12 nm and include cisplatin in an amount of 20 to 300 mg/g. The cancerous sample has a reduced cell viability after the contacting.

18 Claims, 15 Drawing Sheets

(51) Int. Cl.
 *A61K 33/243* (2019.01)
 *A61K 47/02* (2006.01)
 *A61P 35/00* (2006.01)
 *B82Y 5/00* (2011.01)

(52) U.S. Cl.
 CPC .............. *A61K 47/02* (2013.01); *A61P 35/00* (2018.01); *B82Y 5/00* (2013.01)

(56) References Cited

U.S. PATENT DOCUMENTS

2005/0180917 A1 8/2005 Patel
2018/0008614 A1 1/2018 Bilodeau et al.

OTHER PUBLICATIONS

Persano, F., et al., "Halloysite-Based Nanosystems for Biomedical Applications", Clays and Clay Minerals, 2021, 21 total pages.
Sun, T.W., et al., "Templated solvothermal synthesis of magnesium silicate hollow nanospheres with ultrahigh specific surface area and their application in high-performance protein adsorption and drug delivery", Journal of Materials Chemistry B, 2016, 13 total pages.

* cited by examiner

○ (Loading data) —— Freundlich model - - - D-R model ······ Langmuir model

CANCER TREATMENT METHOD WITH NANOCOMPOSITE

CROSS-REFERENCE TO RELATED APPLICATIONS

The present application is a Continuation of U.S. application Ser. No. 18/778,340, now allowed, having a filing date of Jul. 19, 2024.

BACKGROUND

Technical Field

The present disclosure is directed to drug delivery systems and methods, particularly to aluminum silicate nanorods (SNRs) for delivering a drug and a method of preparation thereof.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present disclosure.

Carcinoma, and cancer in general, is a leading cause of death globally and presents an obstacle to human survival worldwide. Researchers estimate that carcinoma accounts for nearly 72% of all formally recorded deaths worldwide, with projections indicating a rise to 75% in the coming years. A plurality of therapies are administered to attempt to combat the persistent and ongoing progress of cancerous cells. Therapies are used to extend the duration and improve the quality of life of individuals with carcinoma; however, most chemotherapeutic medications and therapies also negatively affect healthy cells. The chemotherapeutic medications and therapies may cause serious side effects, especially when administered in high doses. Producing effective and economical medications using biological compounds and harmless carriers is a challenge in developing anticancer drugs. It is important to verify that chemotherapies are not detrimental to the general wellness of a patient. Cisplatin (CPN), sometimes called cis-diamminedichloroplatinum (II), is a commonly administered anticancer medicine that is economical and efficient. It is used as a chemotherapy drug against various types of tumors, including, but not limited to, tumors of testicular cancer, ovarian cancer, head and neck cancer, lung cancer, and bladder cancer. CPN is classified as an alkylating chemotherapy medication that has a cell cycle-nonspecific property. The mechanism of action involves the formation of crosslinks inside the purine part of DNA, leading to the cessation of DNA formation and eventually inducing cellular death [Li, Y. and Lin, W., 2023. Platinum-based combination nanomedicines for cancer therapy. *Current Opinion in Chemical Biology*, 74, 102290]. Further, administering cytostatic medicines often results in certain disadvantages when using CPN for chemotherapy treatment, such as heightened toxicity and nephrotoxicity, among other possible adverse outcomes [R. Oun, Y. E. Moussa, N. J. Wheate, 2018, The side effects of platinum-based chemotherapy drugs: a review for chemists, *Dalton Transactions*, 47 6645-6653]. Researchers have developed numerous efficient modes of administration to mitigate these adverse effects. Various carriers, including lipids, micelles, nanoparticles, polymers, and cryogenics, have been evaluated to counter the side effects of chemotherapies.

Clay minerals, including, but not limited to, kaolinite, vermiculite, montmorillonite, sepiolite, and halloysite, have been identified as effective carriers of common chemotherapies. Clay minerals have stable chemical properties, are safe for patients, and have favorable layered aluminosilicate structures that may exchange ions. The morphological properties of the clay minerals have an impact on their chemical, biological, and physical properties, as the morphology may influence properties such as adsorption capacity, surface area, and extent of active site exposure. Furthermore, clay-based one-dimensional nanostructures (nanotubes) have been developed, an advanced modified form of clay with unique surface area and dispersion properties [M. D. Alqahtani, N. Nasser, M. N. Bin Jumah, S. A. Al Zahrani, A. A. Allam, M. R. Abukhadra, S. Bellucci, 2023, Insight into the morphological properties of nano-kaolinite (nanoscrolls and nanosheets) on its qualification as delivery structure of oxaliplatin: loading, release, and kinetic studies, *Molecules*, 28, 5158]. A process of modifying one-dimensional nanostructures involves facile sonication-prompted chemical exfoliation, followed by scrolling processes, resulting in semicrystalline particles. These particles, composed of scrolled single or multiple clay sheets, exhibit unique surface reactivity, surface area, porous structure, and adsorption capacities. This technique has been applied to produce nanostructures of clay minerals that may exhibit improved biological compatibility, adsorption capacity, oxidation characteristics, surface reactivity, anticancer activity, surface area, and dispersion properties; however, the exfoliation and scrolling of clay minerals have primarily concentrated on kaolinite and bentonite.

Glauconite is a common type of natural clay mineral with the structure K, Na, $(Fe^{3+}, Fe^{2+}, Al, Mg)_2(Si, Al)_4O_{10}(OH)_2$. The structural composition of glauconite includes mixed layers of illite/smectite intercalated units, where the alumina di-octahedral unit sits between two silicon tetrahedron units containing interlayer $K^+$ cations. Glauconite is economical, has a metal-bearing chemical structure, attractive morphology, high surface area, catalytic properties, and good ion exchange capacities; however, present technologies and methods are limited in making advantageous medical use of glauconite, specifically for cancer treatment.

Accordingly, an object of the present disclosure is to provide silicate nanorods (SNRs) developed using natural glauconite minerals that may circumvent the above-stated drawbacks, such as low efficiency, adverse drug side effects, and the expensive nature of present methods and publications.

SUMMARY

In an exemplary embodiment, a method of cytotoxically treating cancer is described. The method includes contacting aluminum silicate nanorods (SNRs) including aluminum, iron, magnesium, oxygen, potassium, and oxygen with a cancerous sample. The aluminum silicate nanorods have a longest dimension of 100 nanometers (nm) to 5500 nm and a diameter of 20 nm to 250 nm. The aluminum silicate nanorods are porous with a pore size of 1 nm to 12 nm and include cisplatin in an amount of 20 to 300 mg/g. The cancerous sample has a reduced cell viability after the contacting.

In some embodiments, the aluminum silicate nanorods are rolled nanosheets of an exfoliated glauconite.

In another exemplary embodiment, a process of making the aluminum silicate nanorods is described. The process includes grinding a glauconite and dispersing and stirring the ground glauconite in a polar solvent for 70 to 75 hours (h). The process of dispersing and stirring breaks intermolecular bonds in the glauconite. The process further includes washing the dispersed glauconite 4 to 6 times for 10 to 30 minutes, each time with methanol to form a methoxy glauconite. The process of immersing and stirring the methoxy glauconite is carried out in an aqueous cetyltrimethylammonium bromide solution for 45 to 50 h at 800 revolutions per minute (rpm) to 1200 rpm to form exfoliated methoxy glauconite layers. The process further includes sonicating the exfoliated methoxy glauconite layers at a power supply of 230 watts (W) to 250 W for 90 to 100 h to form a product. The process of sonicating rolls the exfoliated methoxy glauconite layers into the product. The process further includes filtering, washing the product with deionized water, and drying the product at 50 degrees Celsius (° C.) to 70° C. to form the aluminum silicate nanorods.

In some embodiments, the polar solvent is a 5:95 to 25:75 volume to volume (v/v) ratio mixture of water to dimethyl sulfoxide.

In some embodiments, the process further includes loading the aluminum silicate nanorods with cisplatin.

In some embodiments, the cisplatin is present on an outer surface of the aluminum silicate nanorods.

In some embodiments, cisplatin encapsulates 50 percent to 100% of the outer surface of the aluminum silicate nanorods.

In some embodiments, the cisplatin interacts with the pores and the outer surface of the aluminum silicate nanorods through hydrogen bonding and Van der Waals forces.

In some embodiments, the nanorods are formed by mixing the aluminum silicate nanorods with a cisplatin solution at a pH of 2 to 10.

In some embodiments, the aluminum silicate nanorods are formed by mixing the aluminum silicate nanorods with cisplatin for 0.5 h to 25 h.

In some embodiments, the aluminum silicate nanorods have a saturation loading capacity of 200-350 milligram of cisplatin per gram of nanorod (mg/g).

In some embodiments, the aluminum silicate nanorods have a density of loading receptor value of 12 to 17 mg/g.

In some embodiments, the aluminum silicate nanorods have binding site, and each binding site accommodates 15 to 25 molecules of cisplatin.

In some embodiments, the aluminum silicate nanorods release cisplatin for 190 to 210 h at a pH of 5.4 to 5.6.

In some embodiments, the aluminum silicate nanorods release cisplatin for 100 to 120 h in a solution at a pH of 7.3 to 7.5.

In some embodiments, the aluminum silicate nanorods have a surface area of 120 square meter per gram ($m^2/g$) to 130 $m^2/g$.

In some embodiments, the aluminum silicate nanorods have an average pore diameter of 3 nanometers (nm) to 5 nm.

In yet another exemplary embodiment, the aluminum silicate nanorods have an uptake energy for the cisplatin of −6 kilojoules per mole (kJ/mol) to −2 KJ/mol.

In some embodiments, the cell viability of the cancerous sample is 2% to 5% after 48 h of contacting.

In some embodiments, the cell viability of the cancerous sample is 0.5% to 1.0% after 72 h of contacting.

These and other aspects of the non-limiting embodiments of the present disclosure will become apparent to those skilled in the art upon review of the following description of specific non-limiting embodiments of the disclosure in conjunction with the accompanying drawings. The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure (including alternatives and/or variations thereof) and many of the attendant advantages thereof will be readily obtained as the same becomes better understood by reference to the following detailed description when considered in connection with the accompanying drawings, wherein.

DETAILED DESCRIPTION

Figure 1:
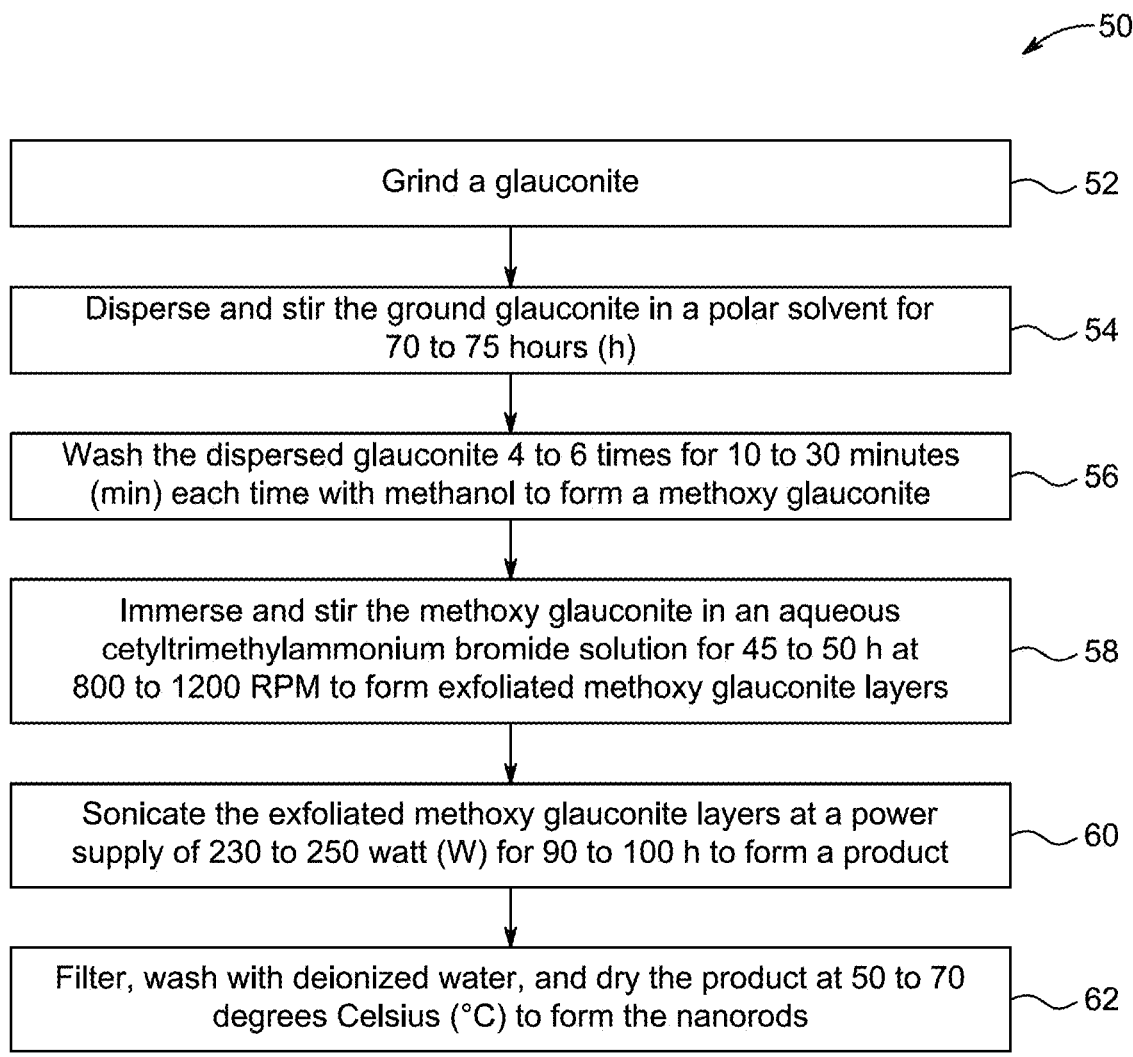
FIG. 1 is a flowchart illustrating a method for making aluminum silicate nanorods, according to certain embodiments.

When describing the present disclosure, the terms used are to be construed in accordance with the following definitions, unless a context dictates otherwise.

Embodiments of the present disclosure will now be described more fully hereinafter with reference to the accompanying drawings wherever applicable, in that some, but not all embodiments of the disclosure are shown. In the following description, it is understood that other embodiments may be utilized, and structural and operational changes may be made without departure from the scope of the present embodiments disclosed herein.

Reference will now be made to specific embodiments or features, examples of which are illustrated in the accompanying drawings. In the drawings, whenever possible, corresponding or like reference numerals will be used to designate identical or corresponding parts throughout the several views. Moreover, references to various elements described herein are made collectively or individually when there may be more than one element of the same type. However, such references are merely exemplary in nature. It may be noted that any reference to elements in the singular may also be constructed to relate to the plural and vice-versa without limiting the scope of the disclosure to the exact number or type of such elements unless set forth explicitly in the appended claims. Further, as used herein, the words "a," "an," and the like generally carry a meaning of "one or more," unless stated otherwise.

Furthermore, the terms "approximately", "approximate", "about," and similar terms generally refer to ranges that include the identified value within a margin of 20%, 10%, or preferably 5%, and any values therebetween. Within the description of this disclosure, where a numerical limit or range is stated, the endpoints are included unless stated otherwise. Also, all values and subranges within a numerical limit or range are specifically included as if explicitly written out.

The use of the terms "include," "includes", "including," "have," "has," or "having" should be generally understood as open-ended and non-limiting unless specifically stated otherwise.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

As used herein, the term "composite material" refers to an amalgamation of two materials each with distinct physical and chemical properties.

As used herein, "nanoparticles (NPs)" are particles having a particle size of 1 nm to 500 nm within the scope of the present disclosure. The nanoparticles may exist in various morphological shapes, such as nanowires, nanocrystals, nanorectangles, nanotriangles, nanopyramids, nanopentagons, nanohexagons, nanoprisms, nanodisks, nanocubes, nanoribbons, nanoblocks, nanobubbles, nanobeads, nanotoroids, nanodiscs, nanobarrels, nanogranules, nanowhiskers, nanoflakes, nanofoils, nanopowders, nanoboxes, nanostars, nanotetrapods, nanobelts, nano-urchins, nanoflowers, and the like, and mixtures thereof.

As used herein, the term "ultrasonication" or "sonication" refers to the process in which sound waves are used to agitate particles in a solution.

As used herein, the term "deionized water" refers to water that has had (most of) the ions removed.

In addition, the present disclosure is intended to include all isotopes of atoms occurring in the present compounds and complexes.

The present disclosure is intended to include all hydration states of a given compound or formula, unless otherwise noted or when heating a material.

Aspects of the present disclosure are directed to aluminum silicate nanorods (SNRs) that were developed from natural glauconite minerals via sonochemical scrolling techniques. The developed SNRs were further evaluated for their potential as a drug delivery system for the anticancer drug, cisplatin (CPN). When compared to conventional anticancer drugs, the SNRs of the present disclosure exhibit biocompatible properties, anticancer activity, and value as a low-cost product with fewer side effects.

Disclosed herein are aluminum SNRs, also referred to as SNRs or, more generally, nanorods. The SNRs include aluminum, iron, magnesium, oxygen, potassium, and oxygen. The SNRs are rolled nanosheets of an exfoliated glauconite. In some embodiments, the nanorods have a longest dimension of 100-5500 nm, 500-5000 nm, preferably 1000-4500 nm, preferably 1500-4000 nm, preferably 2000-3500 nm, and preferably 2500-3000 nm, and a diameter of 20-250 nm, preferably 30-240 nm, preferably 40-230 nm, preferably 50-220 nm, preferably 60-210 nm, preferably 70-200 nm, preferably 80-190 nm, preferably 90-180 nm, preferably 100-170 nm, preferably 110-160 nm, preferably 120-150 nm, and preferably 130-140 nm.

The SNRs porous in nature. Pores may be micropores, mesopores, macropores, and/or a combination thereof. The nanorods are porous with a pore size of 1-12 nm, preferably 2-11 nm, preferably 3-10 nm, preferably 4-9 nm, preferably 5-8 nm, and preferably 6-7 nm. The nanorods have an average pore diameter of 3-5 nm, preferably 3.2-4.8, more preferably 3.5-4.5 nm, and yet more preferably 3.9-4.3 nm. In a preferred embodiment, the nanorods have an average pore diameter of about 4.16 nm. In some embodiments, the nanorods have a surface area of 120-130 meters square per gram ($m^2/g$), preferably 121-129 $m^2/g$, preferably 122-128 $m^2/g$, preferably 123-127 $m^2/g$, and preferably 124-126 $m^2/g$. In a preferred embodiment, the nanorods have a surface area of about 123.7 $m^2/g$.

FIG. 1 illustrates a flow chart of method 50 for making nanorods according to embodiments of the present disclosure. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes grinding a glauconite. Glauconite is a common type of natural clay mineral with the structure K, Na, $(Fe^{3+}, Fe^{2+}, Al, Mg)_2(Si, Al)_4O_{10}(OH)_2$. Glauconite's structural composition consists of mixed layers of illite/smectite intercalated units, where the alumina dioctahedral unit sits between two silicon tetrahedron units that contain interlayer $K^+$ ions. It is a mineral that has extensive natural resources, is cheap, has a metal-bearing chemical structure, attractive morphology, a high surface area, good catalytic properties, and ion exchange capacity. Glauconite is ground to reduce its particle size using any suitable means, for example, ball milling, blending, and the like, using manual methods (e.g., mortar) or machine-assisted methods such as using a mechanical blender and/or any other apparatus known to those of ordinary skill in the art.

At step 54, the method 50 includes dispersing and stirring the ground glauconite in a polar solvent for 70-75 hours (h), preferably 71-74 h, more preferably 72-73 h, and yet more preferably about 72 h. This is carried out to break the intermolecular bonds in the glauconite, preferably the illite units of the glauconite structure. Suitable examples of polar solvents include water, methanol, ethanol, acetone, dimethyl sulfoxide (DMSO), dimethylformamide, dimethylacetamide, isopropanol, and the like, and mixtures thereof. In some embodiments, the polar solvent is a 5:95 to 25:75 (1:19 to 1:3) volume-to-volume (v/v) ratio mixture of water to DMSO, preferably 1:18 to 1:4, preferably 1:17 to 1:5, preferably 1:16 to 1:6, preferably 1:15 to 1:7, preferably 1:14 to 1:8, preferably 1:13 to 1:9, and preferably 1:12 to 1:10. In a preferred embodiment, the polar solvent is 20:80 v/v ratio mixture of water to DMSO. The water may be tap water, distilled water, bi-distilled water, deionized water, deionized distilled water, reverse osmosis water, and/or some other water. In a preferred embodiment, the water is deionized water.

At step 56, the method 50 includes washing the dispersed glauconite 4-6 times, preferably 5 times for 10-30 minutes (min), preferably 11-29 min, preferably 12-28 min, preferably 13-27 min, preferably 14-26 min, preferably 15-25 min, preferably 16-24 min, preferably 17-23 min, preferably 18-22 min, more preferably 19-21 min, and yet more preferably about 20 min each time with methanol to form a methoxy glauconite. In a preferred embodiment, the method 50 includes washing the dispersed glauconite 5 times for 20 min each time with methanol to form a methoxy glauconite.

At step 58, the method 50 includes immersing and stirring the methoxy glauconite in an aqueous cetyltrimethylammonium bromide solution for 45-50 h, preferably 46-49 h, more preferably 47-48 h, and yet more preferably for about 48 h at 800-1200 revolutions per minute (rpm), preferably 950-1150 rpm, preferably 900-1100 rpm, more preferably 950-1050 rpm, and yet more preferably about 1000 rpm to form exfoliated methoxy glauconite layers. Optionally, other surfactants such as sodium deoxycholate SDBS, sodium dodecyl sulfate HTAB, sodium dodecyl benzenesulfonate SDS, hexadecyltrimethylammonium bromide, and Triton X-100, Tween 80, sodium dodecylbenzene sulfonate (SDBS), sodium cholate (SDOC), and/or a combination thereof may be used instead of or in combination with CTAB to form the exfoliated methoxy glauconite layers.

At step 60, the method 50 includes sonicating the exfoliated methoxy glauconite layers at a power supply of 230-250 watt (W), preferably 231-249 W, preferably 232-248 W, preferably 233-247 W, preferably 234-246 W, preferably 235-245 W, preferably 236-244 W, preferably 237-243 W, preferably 238-242 W, more preferably 239-241 W, and yet more preferably about 240 W for 90-100 h, preferably 91-99 h, preferably 92-98 h, more preferably 93-97 h, and yet more preferably 94-96 h to form a product. The sonicating rolls the exfoliated methoxy glauconite layers into the product. In a preferred embodiment, the method 50 includes the method 50 includes sonicating the exfoliated methoxy glauconite layers at a power supply of 240 W for 96 h.

At step 62, the method 50 includes filtering, washing with deionized water, and drying the product at 50-70 degrees Celsius (° C.), preferably 51-69° C., preferably 52-68° C., preferably 53-67° C., preferably 54-66° C., preferably 55-65° C., preferably 56-64° C., preferably 57-63° C., preferably 58-62° C., more preferably 59-61° C., and yet more preferably about 60° C. to form the nanorods. Other suitable techniques for separating the product include centrifugation, internal and external filtration, natural and forced sedimentation, magnetic separation, vacuum filtration, vacuum distillation, chemical conversion, and the like. In a preferred embodiment, filtration was done through a cellulose membrane, such as a Whatman filter paper. The drying can be done by using heating appliances such as hot plates, heating mantles ovens, microwaves, autoclaves, tapes, oil baths, salt baths, sand baths, air baths, hot-tube furnaces, hot-air guns, and the like. In a preferred embodiment, the drying was done using a hot air oven at 60° C.

In an embodiment, the process further includes loading the nanorods with cisplatin (CPN). CPN, sometimes referred to as cis-diamminedichloroplatinum (II), is a commonly administered anticancer medicine that is both affordable and efficient. It is used as a type of chemotherapy against tumors present in various cancers, including testicular cancer, ovarian cancer, head and neck cancer, lung cancer, and bladder cancer. CPN is classified as an alkylating chemotherapy medication that has a cell cycle-nonspecific property. The mechanism of action involves the formation of crosslinks inside the purine part of DNA, leading to the cessation of DNA formation and eventually inducing cellular death. Administering cytostatic medicines often result in certain disadvantages when using CPN for chemotherapy treatment, such as heightened toxicity and nephrotoxicity, among other possible adverse outcomes. In some embodiments, other platins, such as carboplatin, oxaliplatin, and nedaplatin, may be used in combination with cisplatin or in place of cisplatin. In some embodiments, the nanorods may be loaded with any chemotherapeutic drug known in the art.

In some embodiments, the nanorods are formed by mixing the nanorods with a CPN solution at a pH of 2-10, preferably 3-9, preferably 4-8, preferably 5-7, and preferably 5.5-6.5. In some embodiments, the nanorods are formed by mixing the nanorods with CPN for 0.5-25 h, preferably 1-24.5 h, preferably 2-24 h, preferably 3-23 h, preferably 4-22 h, preferably 5-21 h, preferably 6-20 h, preferably 7-19 h, preferably 8-18 h, preferably 9-17 h, preferably 10-16 h, preferably 11-15 h, and preferably 12-14 h.

In some embodiments, the nanorods release CPN for 190-210 h, preferably 191-209 h, preferably 192-208 h, preferably 193-207 h, preferably 194-206 h, preferably 195-205 h, preferably 196-204 h, preferably 197-203 h, preferably 197-202 h, preferably 198-201 h, and preferably 199-200 h at a pH of 5.4-5.6, preferably 5.45-5.55, and more preferably about 5.5. In some embodiments, the nanorods release 15 to 25%, preferably 17 to 23%, preferably 19 to 21%, and preferably about 20% of loaded CPN in 3 to 7 hours, preferably 4 to 6 hours, and preferably about 5 hours at a pH of 5.5. In some embodiments, the nanorods release 45 to 55%, preferably 47 to 53%, preferably 49 to 51%, and preferably about 50% of loaded CPN in 15 to 25 hours, preferably 17 to 23 hours, and preferably 19 to 21 hours at a pH of 5.5. In some embodiments, the nanorods release 70 to 80%, preferably 72 to 88%, preferably 74 to 76%, and preferably about 75% of loaded CPN in 45 to 55 hours, preferably 47 to 53 hours, and preferably 49 to 51 hours at a pH of 5.5. In some embodiments, the nanorods release CPN at a faster rate during hours 1-50 compared to hours 50-200.

In some embodiments, the nanorods release CPN for 100-120 h, preferably 101-119 h, preferably 102-118 h, preferably 103-117 h, preferably 104-116 h, preferably 105-115 h, preferably 106-114 h, preferably 107-113 h, preferably 108-112 h, and preferably 109-111 h in a solution at a pH of 7.3-7.5, preferably 7.35-7.45, and more preferably about 7.4. In some embodiments, the nanorods release 15 to 25%, preferably 17 to 23%, preferably 19 to 21%, and preferably about 20% of loaded CPN in 2 to 6 hours, preferably 3 to 5 hours, and preferably about 4 hours at a pH of 7.4. In some embodiments, the nanorods release 45 to 55%, preferably 47 to 53%, preferably 49 to 51%, and preferably about 50% of loaded CPN in 10 to 15 hours, preferably 11 to 14 hours, and preferably 12 to 13 hours at a pH of 7.4. In some embodiments, the nanorods release 70 to 80%, preferably 72 to 88%, preferably 74 to 76%, and preferably about 75% of loaded CPN in 20 to 30 hours, preferably 22 to 28 hours, and preferably 24 to 26 hours at a pH of 7.4. In some embodiments, the nanorods release CPN at a faster rate during hours 1-30 compared to hours 30-200.

In some embodiments, the nanorods include CPN in an amount of 20-300 mg/g, preferably 30-290 mg/g, preferably 40-280 mg/g, preferably 50-270 mg/g, preferably 60-260 mg/g, preferably 70-250 mg/g, preferably 80-240 mg/g, preferably 90-230, preferably 100-220 mg/g, preferably 110-210 mg/g, preferably 120-200 mg/g, preferably 130-190 mg/g, preferably 140-180 mg/g, and preferably 150-170 mg/g. In a preferred embodiment, the nanorods include CPN in an amount of about 100 mg of CPN per g of the nanorods.

In some embodiments, the CPN is present on the outer surface of the nanorods. In some embodiments, the CPN encapsulates 50-100 percent (%), preferably 55-95%, preferably 60-90%, preferably 65-85%, and preferably 70-80% of the outer surface of the nanorods. The CPN interacts with the pores and the outer surface of the nanorods through hydrogen bonding and van der Waals forces. In some embodiments, the CPN penetrates the outer surface of the nanorods and is in pores of the nanorods. In some embodiments, the pores may be on an inner surface and/or outer surface of the nanorods.

In some embodiments, the SNRs have a saturation loading capacity of 200-350 milligram of CPN per gram of nanorod (mg/g), preferably 210-340 mg/g, preferably 220-330 mg/g, preferably 230-320 mg/g, preferably 240-310 mg/g, preferably 250-300 mg/g, more preferably 260-290 mg/g, and yet more preferably 270-280 mg/g. In a preferred embodiment, the SNRs have a saturation loading capacity of about 283.7 mg/g. In some embodiments, the nanorods have an uptake energy for the CPN of −6 to −2 kilojoules per mole (KJ/mol), preferably −5 to −3 KJ/mol, and more preferably −5 to −4 KJ/mol. In a preferred embodiment, the nanorods have an uptake energy for the CPN of about −4.3 KJ/mol.

In some embodiments, the SNRs have a density of loading receptor value of 12-17 mg/g, preferably 13-16 mg/g, and more preferably 14-15 mg/g. In a preferred embodiment, the SNRs have a density of loading receptor value of 14.5 mg/g. In some embodiments, the nanorods have binding sites, and each binding site accommodates 15-25 molecules of CPN, 15-25, preferably 16-24, preferably 17-23, more preferably 18-22, and yet more preferably 19-21 molecules of CPN. In a preferred embodiment, the nanorods have a binding site, and each binding site accommodates about 20 molecules of CPN.

In an embodiment, a method of cytotoxically treating cancer is described. The method includes contacting the SNRs, preferably the CPN-loaded SNRs, at a concentration of 0.5-2 μg/mL, preferably 0.75-1.75 μg/mL, and preferably 1-1.5 μg/mL with a cancerous sample. In a preferred embodiment, the method includes contacting the CPN-loaded SNRs with the cancerous sample at a concentration of 1 μg/mL. The cancerous sample may be a cell line, a group of cells, and/or a subject with a cancerous mass. In an example, the cell line is a HeLa cell line. After contact with the SNRs or CPN-loaded SNRs, the cancerous sample has reduced a cell viability. In some embodiments, the cell viability of the cancerous sample is about 2-5%, preferably 2.5-4%, and more preferably 3-3.5% after 48 h of contact. In a preferred embodiment, the cell viability of the cancerous sample is about 3.2% after 48 h of contact. In some embodiments, the cell viability of the cancerous sample is about 0.5-1.0%, preferably 0.6-0.95%, and more preferably 0.7-0.9% after 72 h of contact. In a preferred embodiment, the cell viability of the cancerous sample is about 0.87% after 72 h of contact. In some embodiments, the CPN-loaded SNRs may be used as a treatment for any known cancer in the art and/or any known disease and illness in the art.

In some embodiments, the CPN-loaded SNRs may be administered in a treatment plan as a single dose or multiple individual divided doses. In some embodiments, the CPN-loaded SNRs may be administered orally, through a nasal passage, intravenously, sublingually, buccally, subcutaneously, intramuscularly, vaginally, rectally, through an inhalation route, a combination thereof, and/or any other administration methods known in the art. In some embodiments, the CPN-loaded SNRs are administered at various dosages (e.g., a first dose with an effective amount of 50 mg/kg and a second dose with an effective amount of 10 mg/kg). In some embodiments, the interval of time between the administration of the CPN-loaded SNRs and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the CPN-loaded SNRs is administered once daily for at least 2 days, 5 days, 6 days, or 7 days. In certain embodiments, the CPN-loaded SNRs and one or more additional therapies are administered less than 1 day,

EXAMPLES

The disclosure will now be illustrated with working examples, which are intended to illustrate the working of the disclosure and not intended to restrictively imply any limitations on the scope of the present disclosure, as many variations thereof are possible without departing from the spirit and scope of the present disclosure. The following examples demonstrate a drug delivery system and method of preparation thereof. The examples are provided solely for illustration and are not to be construed as limitations of the present disclosure.

Example 1: Synthesis of Silicate Nanorods (SNRs)

About 40 grams (g) of ground glauconite mineral was dispersed in about 200 millilitres (mL) of diluted dimethyl sulfoxide (DMSO) solution, having about 80% DMSO and 20% water, under vigorous stirring for 72 hours (h). the vigorous stirring process includes breaking intermolecular bonds found in clay layers, specifically, the illite units of the glauconite structure. Following this, the formed product was washed five times with methanol, with each washing run lasting approximately 20 minutes, resulting in the formation of methoxy glauconite (MX/G) with organophilic properties. The obtained MX/G fractions were immersed in aqueous solutions of cetyltrimethylammonium bromide (CTAB), about 60 g CTAB in about 200 mL water, at room temperature. Solutions comprising the MX/G fractions in the aqueous solutions of CTAB were continuously stirred for 48 hours (h) at 1000 revolutions per minute (rpm) to exfoliate the glauconite sheets. The CTAB serves as an expansion reagent. Subsequently, a 240 W power supply sonication source treated the system for 96 h, promoting the rolling of exfoliating layers into glauconite rods. The product (silicate nanorods (SNRs)), after extraction by filtration via Whitman paper, was washed multiple times with distilled water and dried at 60 degrees Celsius (° C.).

Example 2: Loading properties of cisplatin (CPN)

The loading characteristics of the SNRs as potential CPN vehicles were assessed. The implications of various loading settings, such as pH levels ranging from 3 to 8, loading intervals spanning from 1 to 24 h, and drug concentrations from 100 milligrams per liter (mg/L) to 700 mg/L, were analyzed. The SNRs nanoparticles were mixed with CPN fluids using a vortex rotator apparatus. After completing the loading operations, CPN-containing SNR particulates were separated from the CPN fluids using Whitman filter paper. A UV-Vis spectrophotometer was employed at a determination wavelength of 300 nanometres (nm) to quantify the CPN concentrations in the collected filtrates. The loading efficiencies were established using Equation (Eq.) 1. The loading examinations were conducted as three separate experiments, and the calculations and graphs were constructed based on the average results obtained from these tests with standard deviations of less than 3.3%.

$$\text{Loaded drug}\left(\frac{\text{mg}}{\text{g}}\right) = \frac{(\text{Initial concentration} - \text{Residual concentration})}{\text{Carrier weight}} \quad (1)$$

Example 3: In-Vitro Release Studies

The releasing behaviors of CPN out of the SNRs particulates was investigated at a releasing temperature of 37.5° C. The releasing responses of CPN were monitored using pH 4.5 acetate buffered solutions and pH 7.4 phosphate buffered solutions. To conduct the release experiments, pre-measured quantities of the SNRs encapsulating CPN (100 mg/g) were separately submerged into 250 mL of various buffering solutions and were pulverized using Distek dissolving equipment. The vessel was rotated at a velocity of 200 rpm for up to 200 h. 3 mL of the buffered solution from the device vessels were extracted at regular intervals to measure the released CPN concentrations. The CPN medication was analyzed using a UV-visible spectrophotometer at a wavelength of 300 nm. To ensure consistent volumes of the buffering agents throughout the in vitro diffusing time frames, the vessels were refilled with the 3 mL samples of the buffers after the detection round of each drug. The release examinations were conducted three times, using the average results as the foundation for calculations and the creation of the graphs. The measured CPN levels were used to determine the percentages of released medicine, following the formula in Eq. 2.

$$\text{Drug release (\%)} = \frac{\text{Amount of released drug}}{\text{Amount of loaded drug}} \times 100 \quad (2)$$

Example 4: In-Vitro Cytotoxicity

The effects on cells of CPN-loaded SNRs have been compared to those of CPN using HeLa cells from people with cervical epithelial cancer. The HeLa cells were cultivated in RPMI 1640 medium enriched with 10% fetal bovine serum (FBS), 2 millimolar (mM) of L-glutamine, and 1% penicillin-streptomycin. To facilitate the antiproliferation experiment, the HeLa cells were placed on 96-well plates with a density of 10,000 cells per well, with each well containing 100 microliters (μL) of media. The medium diluted the medication under study to achieve cytostatic concentrations of 0.50 g/mL and 1.00 g/mL (pH 6.8 to 7.4). The samples gathered were stored in a controlled environment at a temperature of 37±0.2° C. and further exposed to the HeLa cells. The optical densities of each sample were determined at a wavelength of 450 nm and a plurality of time intervals. The level of proliferation inhibition (N %) induced by the investigated medications was determined using Equation 3.

$$N\% = \frac{N_{ex}}{N_c} \times 100 \quad (3)$$

where, $N_{ex}$ represents the mean quantity of cells throughout the group being investigated, and $N_c$ represents the mean quantity of cells within the control group.

Figure 2:
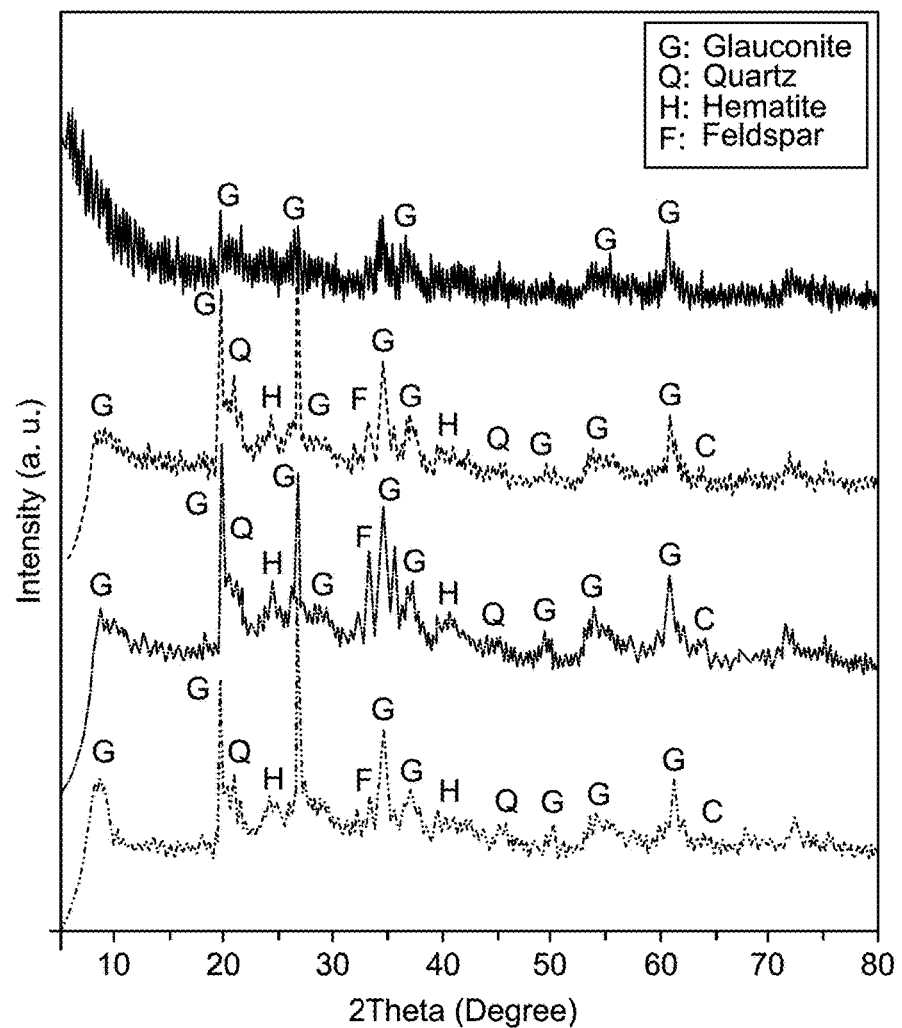
FIG. 2 shows X-ray diffraction (XRD) patterns of raw glauconite, dimethyl sulfoxide (DMSO) intercalated glauconite, methoxy glauconite, and silicate nanorods (SNRs), according to certain embodiments.

Example 5: Characterization of the Carrier Via X-Ray Diffraction (XRD) Analysis The structural modifications and the dominant crystal phases were assessed based on the XRD patterns of the raw glauconite, the synthetic SNRs, and the intermediate phases. The recognized pattern of raw glauconite demonstrates the existence of glauconite as the dominant phase in addition to some impurities, which included quartz, calcite, feldspar, and hematite, as shown in FIG. 2. The identified glauconite form is represented by a 1 M-glauconite poly-type with a well-ordered crystalline structure of an ISII ordered type and is characterized by a high $K_2O$ content and slight swelling properties. The identification of glauconite has been established by analyzing XRD peaks (8.67°, 19.72°, 26.7°, 34.78°, 37.17°, and) 61.31° with a basal spacing of 10.18 angstrom (Å), as shown in FIG. 2. After the modification of the glauconite with DMSO, the obtained XRD pattern demonstrates a deviation in the peaks of glauconite (8.01°, 19.54°, 26.5°, 34.5°, 36.8°, and 61.1°), as shown in FIG. 2. This supports the distortion in the structural units of glauconite after the dispersion of glauconite in DMSO step and the expected intercalation of the silicate layers with the DMSO organic molecules. This was also signified by the detected increment in the basal spacing that expanded to 11.2° C., demonstrating the swelling effect of the intercalated DMSO. Similar observations were detected during evaluation of the XRD pattern of methoxy glauconite. The XRD peaks deviated to lower positions (7.47°, 19.52°, 26.5°, 34.4°, and) 35.57°, as shown in FIG. 2. This was also associated with an expansion effect on the silicate layers of glauconite, which appeared in the rise in basal spacing to 11.81 Å. Regarding synthetic glauconite nanorods, the resulting pattern supports destruction of the structure units of glauconite and partial amorphization of its structure (FIG. 2). The diffraction peaks of glauconite were reduced extensively, and the main peak around 2θ of about 8° disappeared. This observation supports the occurrence of exfoliation and separation throughout the multilayered units, leading to the development of a semi-crystalline form.

Figure 3A:
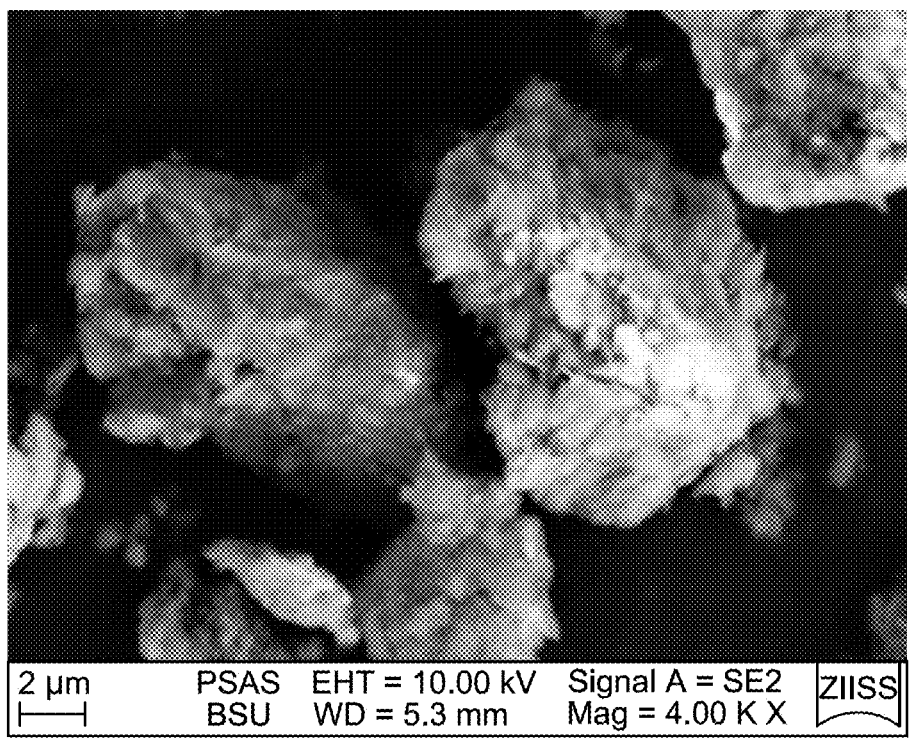
FIG. 3A is a scanning electron microscopy (SEM) image of raw glauconite, according to certain embodiments.
Figure 3B:
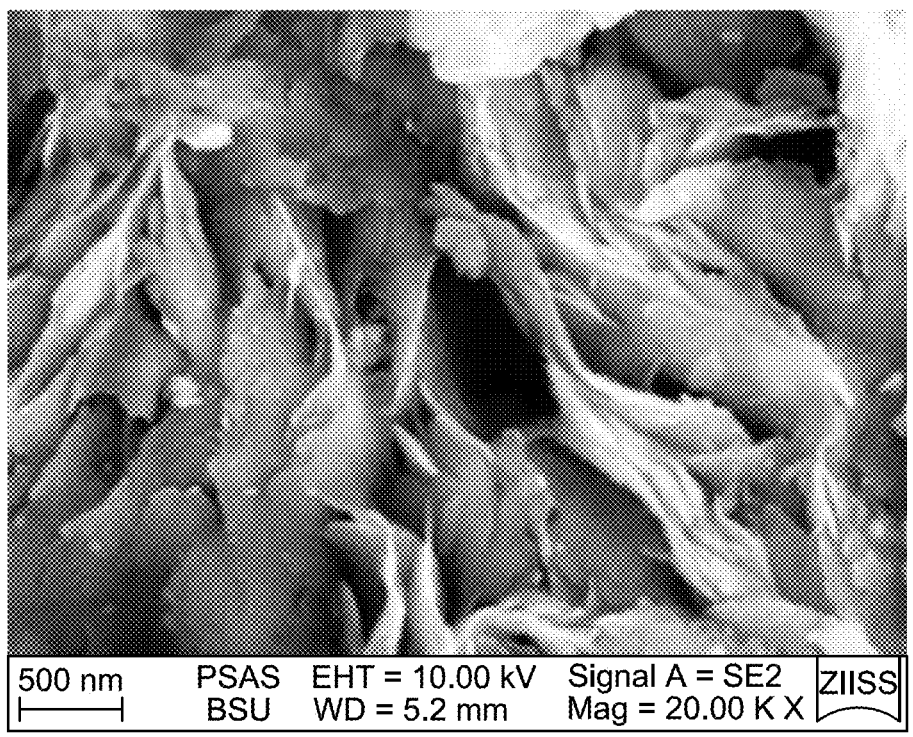
FIG. 3B is an SEM image of DMSO intercalated glauconite, according to certain embodiments.
Figure 3C:
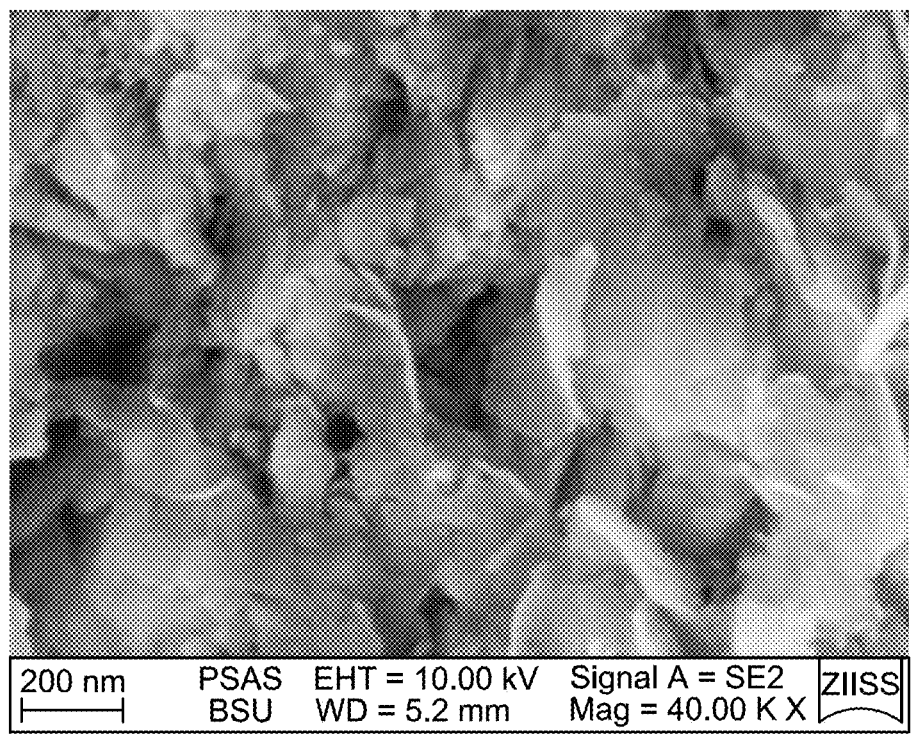
FIG. 3C is an SEM image of methoxy glauconite, according to certain embodiments.
Figure 3D:
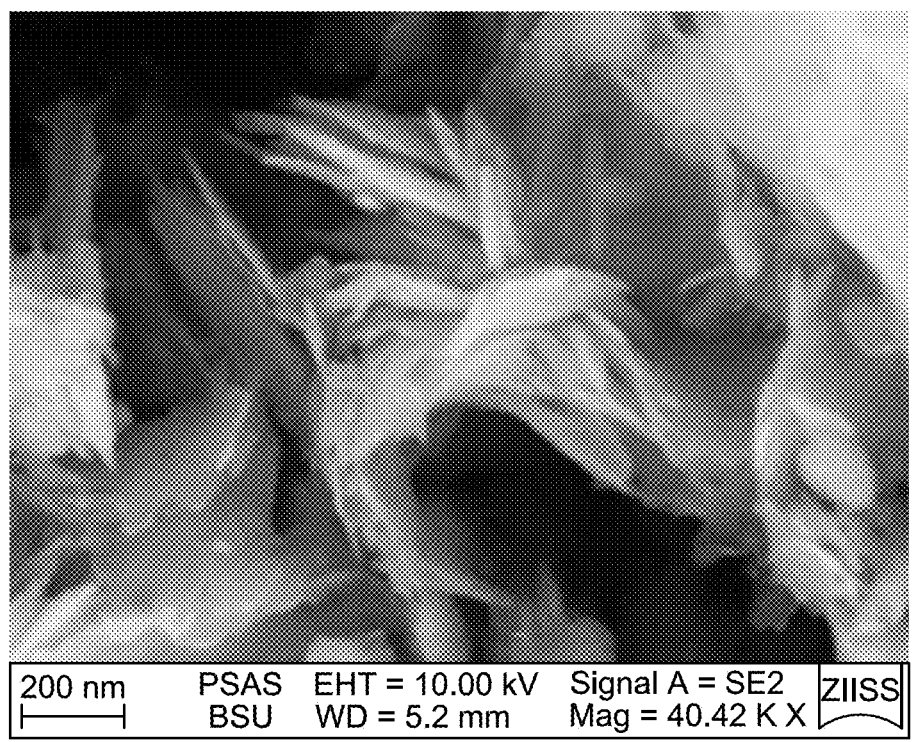
FIG. 3D is an SEM image of cetyltrimethylammonium bromide (CTAB) intercalated glauconite, according to certain embodiments.
Figure 3E:
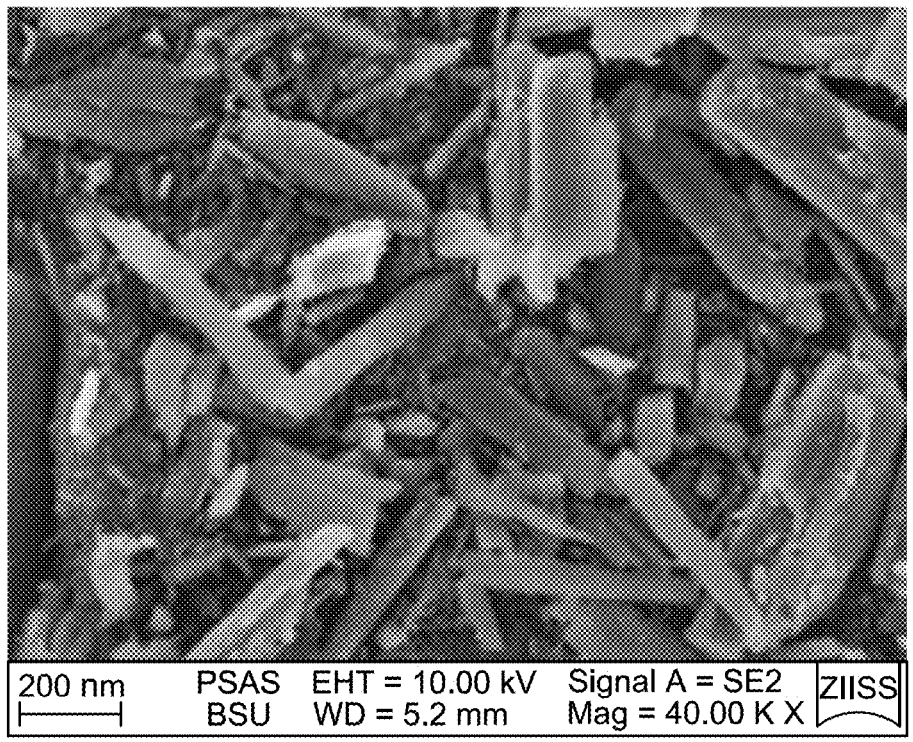
FIG. 3E is an SEM image of the SNRs with a scale of 200 nanometers (nm), according to certain embodiments.
Figure 3F:
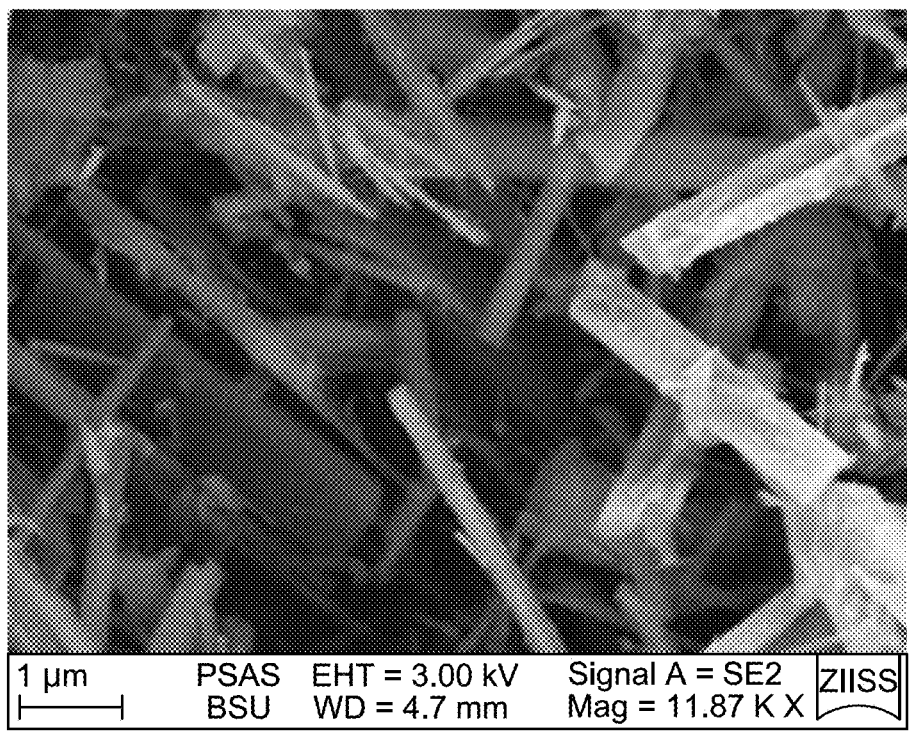
FIG. 3F is an SEM image of the SNRs with a scale of 1 micrometer (μm), according to certain embodiments.

Example 6: Scanning Electron Microscopy (SEM) Analysis and High-Resolution Transmission Electron Microscopy (HRTEM) Analysis The changes in morphological features during the production of the glauconite nanorods were observed by scanning electron microscopy (SEM) and high-resolution transmission electron microscopy (HRTEM), as shown in FIGS. 3A-3F and FIGS. 4A-4F, respectively. The starting glauconite shows the common massive and agglomerated form of glauconite with stacked and compacted layers, as shown in FIG. 3A. The intercalation of the layers with DMSO molecules caused exfoliation of the glauconite layers, which separated from each other effectively (FIG. 3B). Exfoliation of the glauconite layers further increased after the incorporation of the methanol molecules, and the glauconite samples appeared as single layers overlaying each other (FIG. 3C). During an initial stage of the scrolling step with the incorporation of CTAB molecules, the separated glauconite layers exhibited a slight bending and appeared in a curvature form (FIG. 3D). By the end of the scrolling and the modification steps in the existence of the sonication source, the sample reflects a complete change in the morphology to be in rod-like structures instead of the flaky form, shown in FIGS. 3E-3F. The obtained glauconite rob-like structure exhibits a length within the range of 150 nm up to 5 µm and a diameter within the range of about 25 nm up to 200 nm.

Figure 4A:
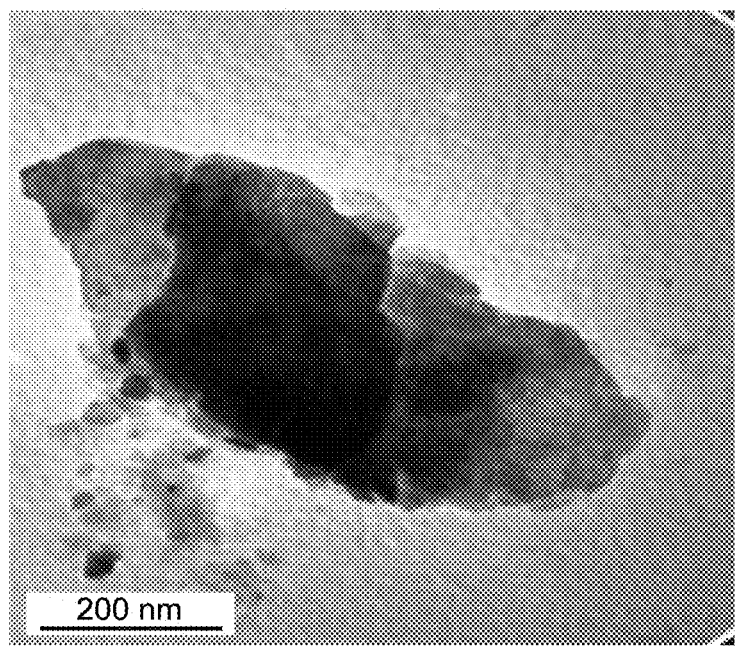
FIG. 4A is a high-resolution transmission electron microscopy (HRTEM) image of raw glauconite, according to certain embodiments.
Figure 4B:
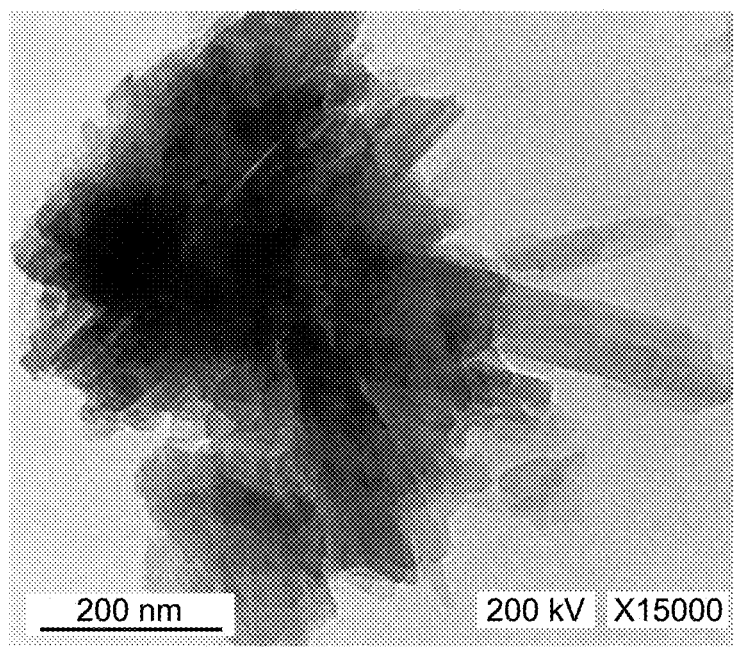
FIG. 4B is an HRTEM image of an initially scrolled glauconite, according to certain embodiments.
Figure 4C:
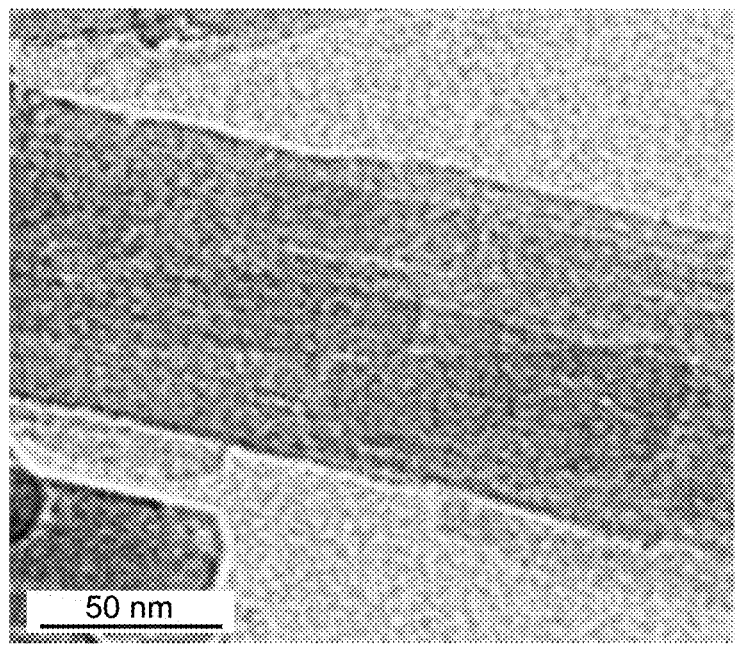
FIG. 4C is an HRTEM image of an initially scrolled glauconite with a scale of 50 nanometers (nm), according to certain embodiments.
Figure 4D:
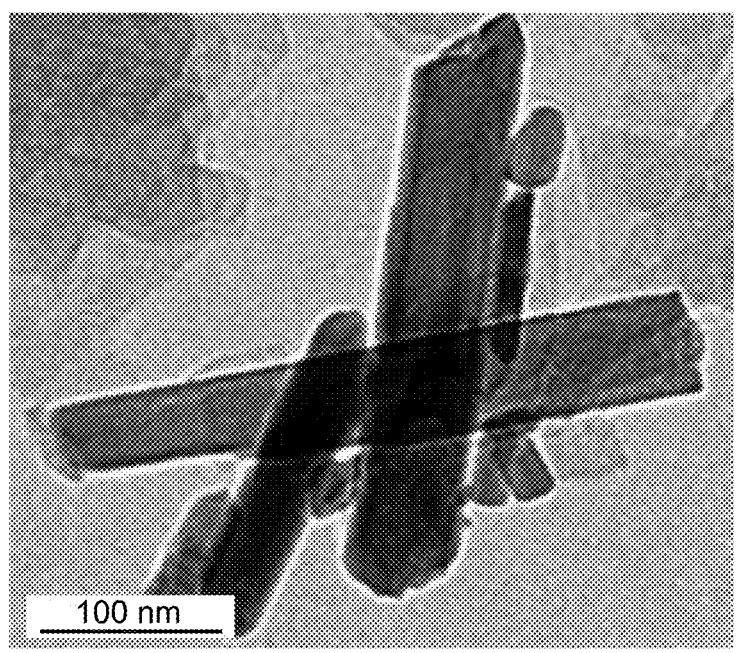
FIG. 4D is a first HRTEM image of the SNRs after sonication treatment with a scale of 100 nm, according to certain embodiments.
Figure 4E:
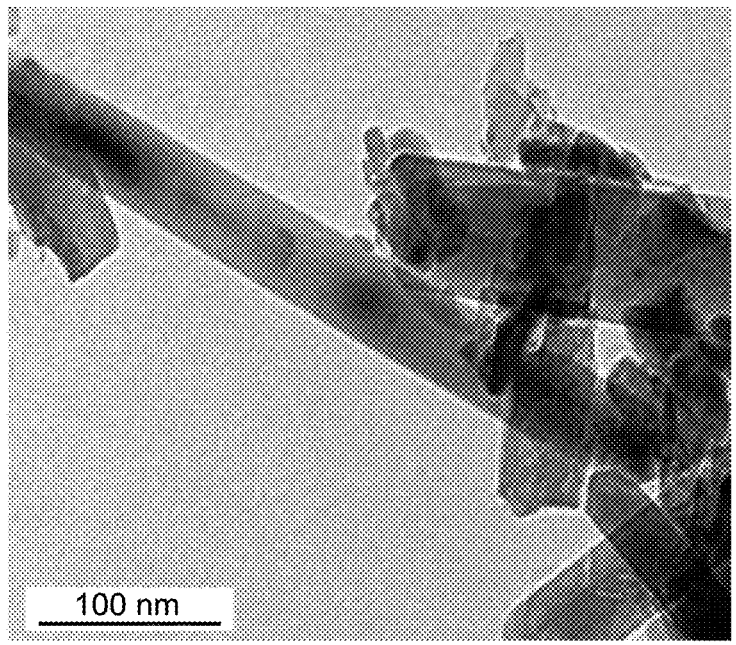
FIG. 4E is a second HRTEM image of the SNRs after sonication treatment with a scale of 100 nm, according to certain embodiments.
Figure 4F:
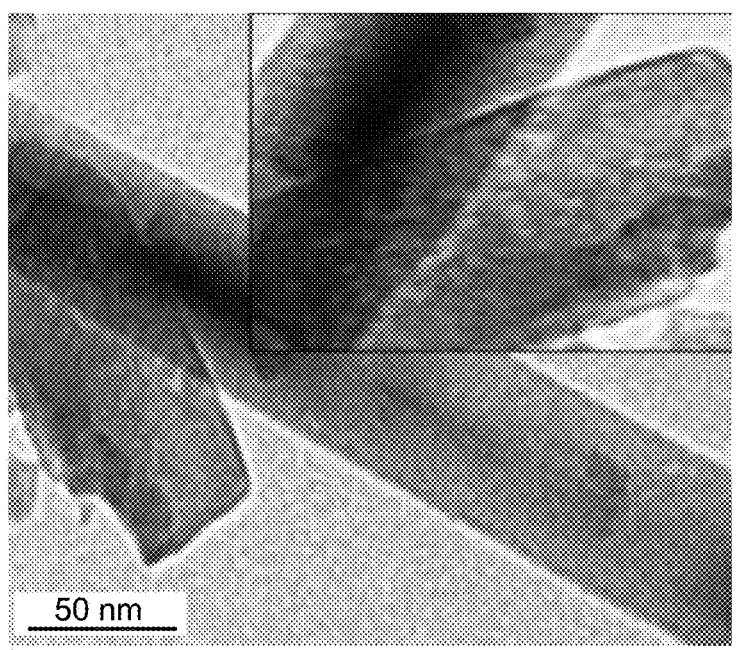
FIG. 4F is an HRTEM image of the SNRs after sonication treatment with a scale of 50 nm, according to certain embodiments.

The recognized HRTEM images of the assessed samples are shown in FIGS. 4A-4F, confirming the detected morphological observations. The glauconite platelets appear as elliptical grains without marked internal properties (FIG. 4A). The intercalated CTAB molecules made the glauconite grains peel off and start to roll, further turning into a multilayered, rod-like nanostructure with clear lattice finger structures (FIG. 4B & FIG. 4C). The extensive scrolling process, especially under the sonication effect, causes a condensation effect on the formed rod structure in a smooth cylindrical form, suggesting separated scrolling of each layer into a single rod, as shown in FIGS. 4D-4F. The images on the surface of the obtained final rods reflect their highly porous properties, which give the structure a ribbon-like morphology. Such morphological features are associated with an increase in the surface area of the structure and its porosity, which induce favorable properties for its qualification to be applied as an effective adsorbent for different species of dissolved water pollutants.

Example 7: Fourier-Transform Infrared (FTIR) Analysis

Figure 5:
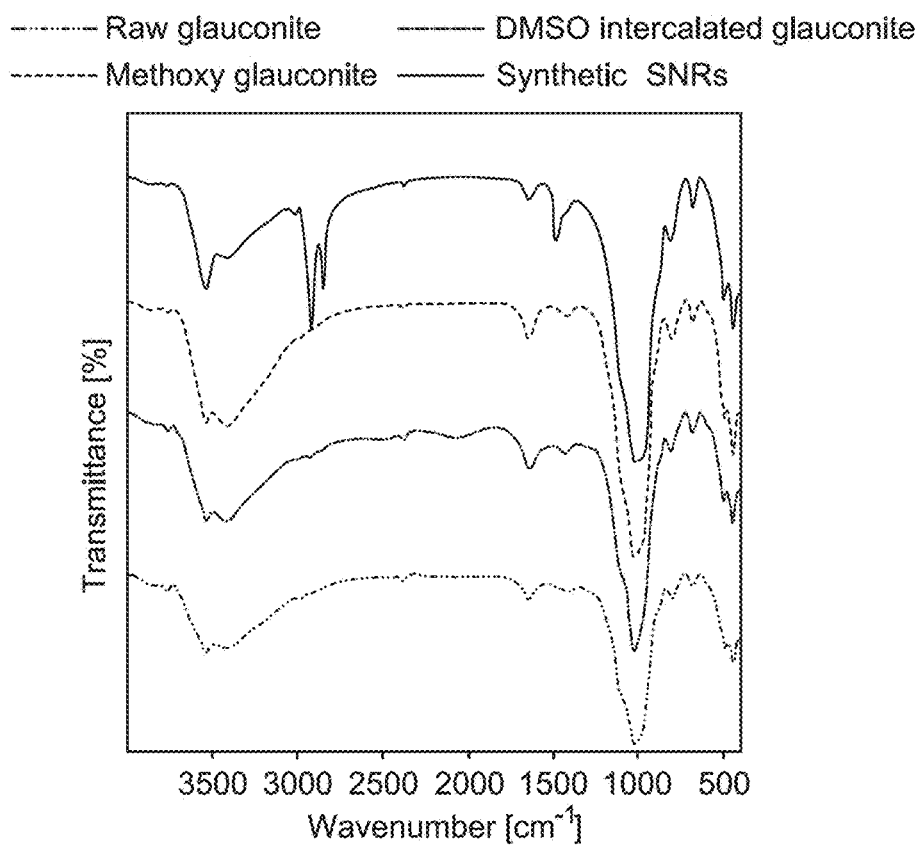
FIG. 5 shows Fourier transform infrared (FTIR) spectra of raw glauconite, DMSO intercalated glauconite, methoxy glauconite, and the SNRs, according to certain embodiments.

The changes in the chemical functional groups during the synthesis steps were followed based on the observed FTIR spectra of the raw glauconite, the synthetic SNRs, and the intermediate structures, as shown in FIG. 5. The obtained spectra display the composition of raw glauconite as a clay mineral of aluminosilicate structure. The identification of the corresponding bands of Si—O—Si, Fe—OH, Si—O, Si—O—Fe, Si(Al)—O—Si, and OH groups in the raw glauconite is shown in FIG. 5. The detected hydroxyl groups around 3500 $cm^{-1}$ were assigned to either adsorbed water or metal hydroxides within the glauconite structure; however, the identified hydroxyl groups corresponding to the absorption band around 1600 $cm^{-1}$ signify the interlayer free water molecules. Further, the recognized bands around 800 $cm^{-1}$ and 490 $cm^{-1}$ display enrichment of the glauconite with iron. Furthermore, both DMSO intercalated glauconite and methoxy glauconite show similar bands to that of raw glauconite with no detectable bands related to the organic structures of methanol or DMSO.

Figure 6:
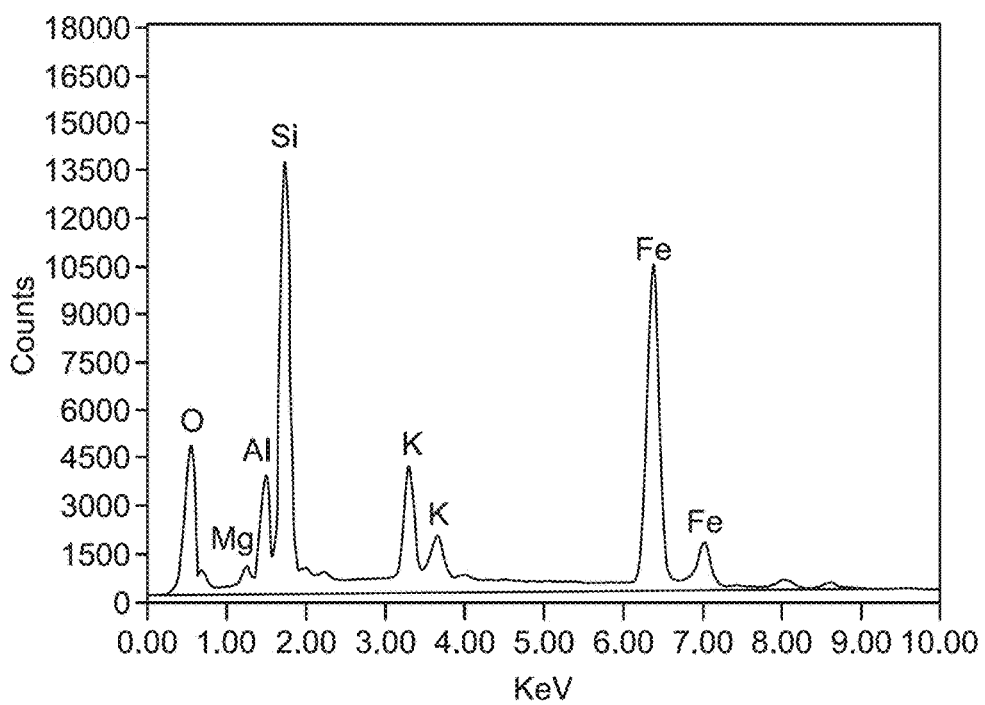
FIG. 6 depicts an energy dispersive X-ray (EDX) spectrum of the SNRs and corresponding elemental composition, according to certain embodiments.

There is a slight fluctuation in the locations of the primary matching bands of the basic functional groups, which may validate the structural effect of the intercalated organic molecules of DMSO and methanol on the structural units of glauconite. Furthermore, there is splitting for the identification band of Si(Al)—O—Si around 1000 $cm^{-1}$. This validates the distortion of the glauconite structural units (octahedron and tetrahedron units) as a result of the partial swelling and exfoliation of silicate layers. After the formation of SNRs, the absorption bands of the main structural units of glauconite deviated at a high rate. Moreover, the splitting of the identification band of Si(Al)—O—Si around 1000 $cm^{-1}$ increased to a degree, supporting an increment in distortion and degree of exfoliation degree. In addition, new bands were detected at 1475 $cm^{-1}$, 2850 $cm^{-1}$, and 2919 $cm^{-1}$ signifying the organic structure of the CTAB molecules that were used during the exfoliation and scrolling processes. The FTIR findings of the SNRs agree with the elemental contents that were determined relying upon an energy dispersive X-ray (EDX) analysis, as shown in FIG. 6. The primary elements of the silicate structures were detected as O, Si, Fe, and K. An increase in the iron (Fe) content after the scrolling process of glauconite into the SNRs reflect the strong diffusion of the structural ion element or iron oxide impurities during the exfoliation and extensive destruction of the glauconite silicate units.

Example 8: Textural Analysis

Figure 7A:
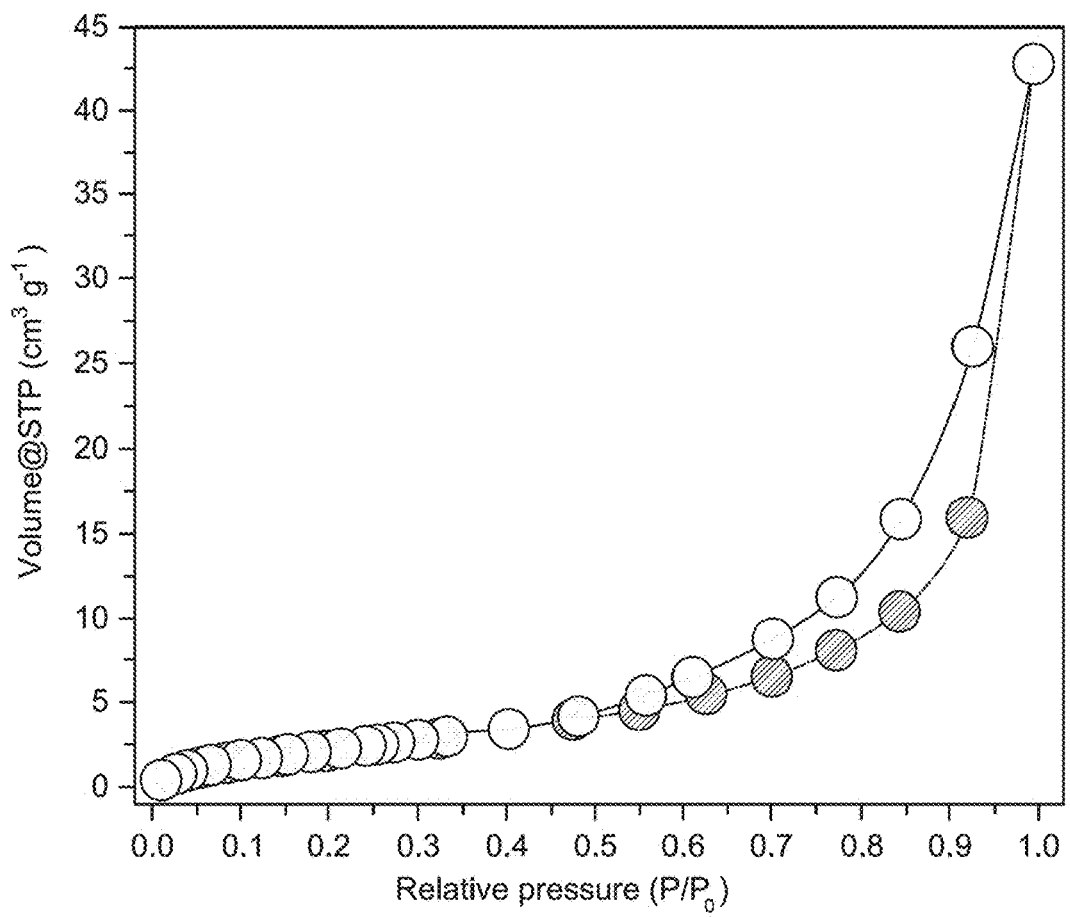
FIG. 7A is a graph depicting the nitrogen adsorption/desorption isotherm curve of the SNRs, according to certain embodiments.
Figure 7B:
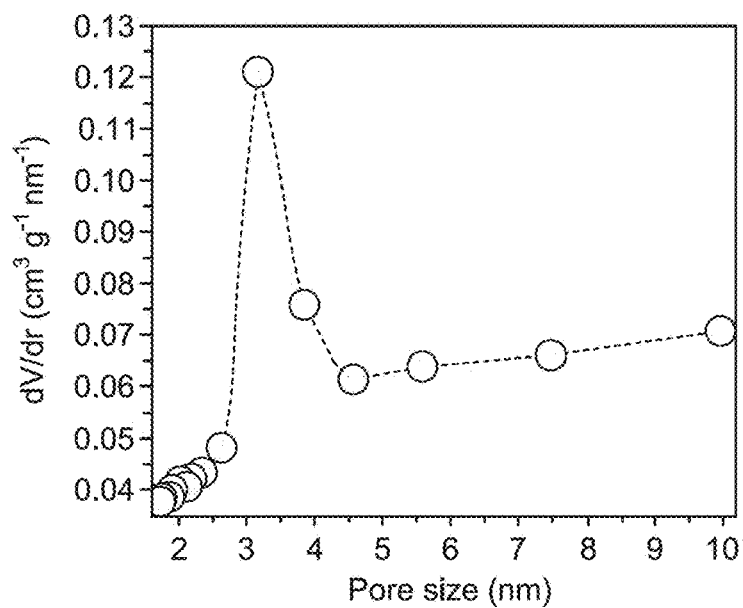
FIG. 7B is a graph depicting pore size distribution properties of the SNRs, according to certain embodiments.

The textural properties of the synthetic SNRs were assessed in terms of porosity and surface area properties based on the obtained $N_2$ adsorption/desorption isotherm curve, as shown in FIG. 7A. The observed curve displays an IV isotherm type with a hysteresis loop of H3 type, as shown in FIG. 7A, with a pore size distribution shown in FIG. 7B. This supports the nanoporous (mesoporous) properties of the synthetic SNRs, which are associated with the evacuation and/or filling of tubular or cylindrical nanopores via capillary condensation mechanisms. The measured surface area of the SNRs is 123.7 $m^2/g$. Further, the SNRs particles display pore sizes ranging from 1.5 nm to 10 nm with an average pore diameter of 4.16 nm, which supports the mesoporous structure.

Example 9: Drug Loading Properties and Effect of Loading Duration

Figure 8A:
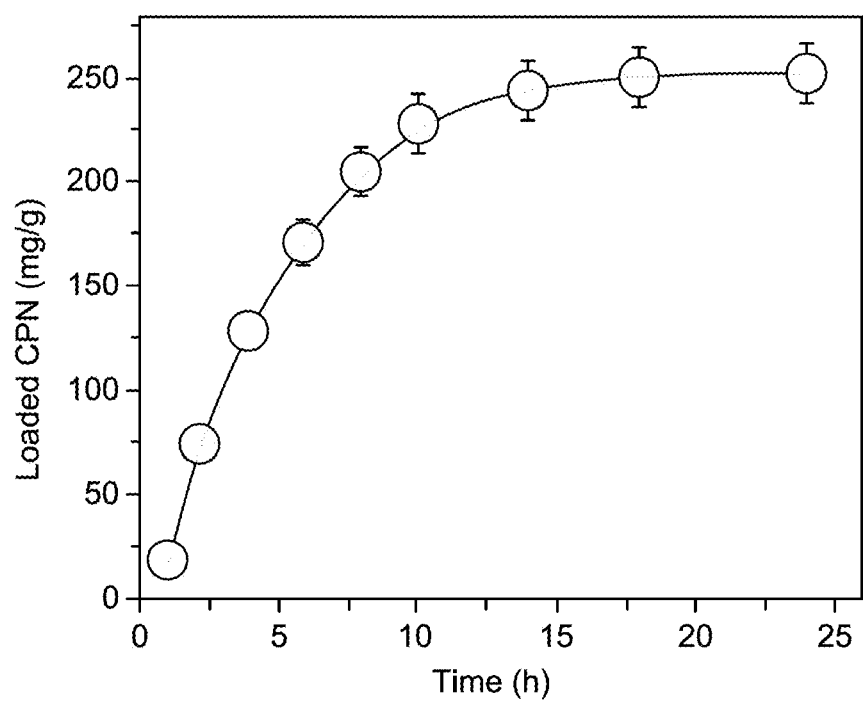
FIG. 8A is a graph depicting the effect of loading duration of CPN into the SNRs, according to certain embodiments.

The impact of varying time durations on the loading quantities of CPN in the SNRs was assessed with time frames ranging from 1 to 24 hours, with a dose of 20 mg, a CPN content of 200 mg/L, a pH of 9, an ambient temperature of 25° C., and an overall volume of 50 mL. The CPN loading characteristics of the SNRs reveal a rise in both the measured rate of loading and the total quantity loaded, in mg/g, whenever the interaction duration is progressively extended, as shown in FIG. 8A. A rise in loading behavior of the SNRs was detected at a time of 10 hours and above. The CPN rate of loading and the loaded amount remain relatively stable or exhibit little variation following the loading interval of 10 hours. These stable loading characteristics confirm the equilibration behaviors of the carriers that were evaluated (251.7 mg/g). During the early loading stages, the SNRs interfaces displayed an elevated proportion of active and unoccupied sites. This resulted in an elevated loading rate alongside a rapid increase in the quantity of CPN entrapped. As the time frame of the loading increases, CPN progressively occupies the available sites of the SNRs. The occupation of available sites leads to the depletion of the effective sites and a decline in their potential to be filled with other adsorbed molecules. Consequently, loading rates for CPN decreased after a period, leading to a reduction in the practical activities of these carriers. Once all the readily accessible sites were filled with CPN, the equilibrium levels of the SNRs were established.

Figure 8B:
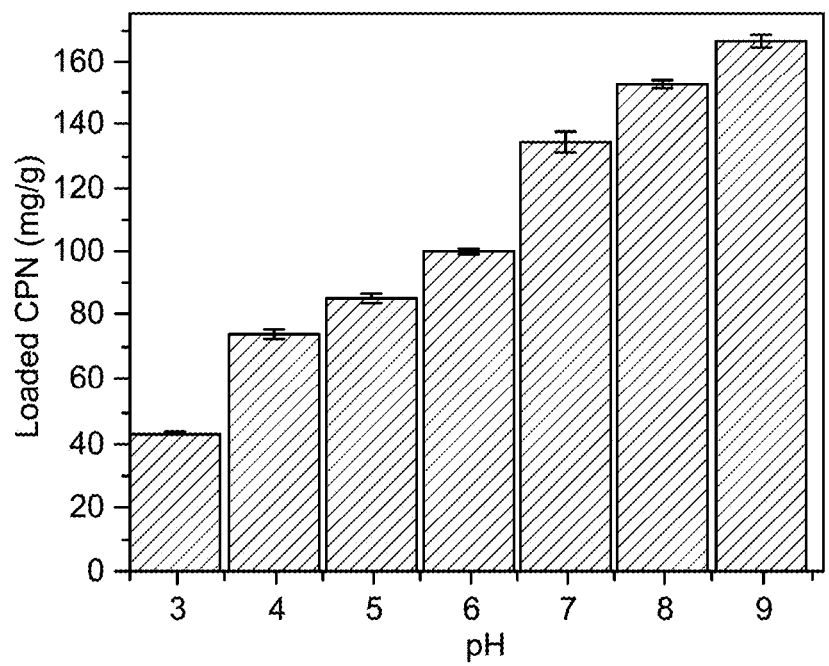
FIG. 8B is a graph depicting the effect of pH on the loading of cisplatin (CPN) onto the SNRs, according to certain embodiments.

Example 10: Effect of Loading pH pH adjustment of solutions in which the drug cisplatin (CPN) is loaded into the SNRs affects the charge densities across the exteriors of SNRs, along with modifications in the species of the ionized CPN present. The influence of pH on the loading behavior of CPN onto the SNRs was determined within a pH range of 3 to 9. The experiments were performed at a dose of 20 mg, a CPN content of 200 mg/L, a time of 120 minutes, a temperature of 25° C., and an overall volume of 50 mL. The loading quantities of CPN across the SNRs expanded from pH 3 (43.5 mg/g) to pH 9 (166.4 mg/g), as shown in FIG. 8B. The loading techniques for CPN onto the SNRs were preferred under alkaline situations. In general, the pH of the solution may affect the ionizing behavior of the solution soluble CPN compound and the exterior charges throughout SNRs. Under an acidic setting, the CPN molecules have positive charges and show competing and electrostatic repulsive tendencies towards the hydronium ions, which are present across the exterior SNRs.

Example 11: Effect of CPN Concentration

Figure 8C:
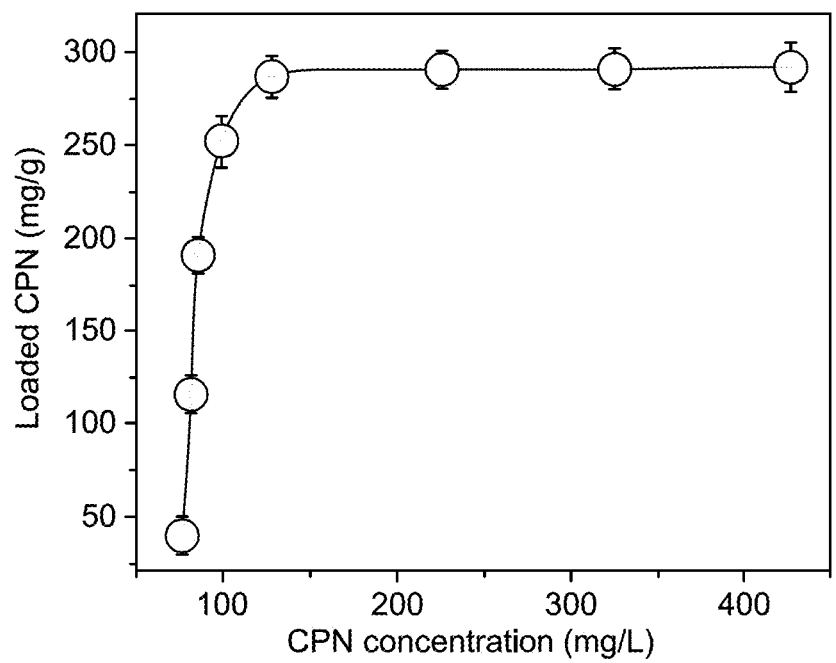
FIG. 8C is a graph depicting the effect of starting concentration on the loading of CPN into the SNRs, according to certain embodiments.

The impact of the starting level of CPN on the encapsulation properties of the SNRs was investigated with a dose of about 20 mg, a time frame of 24 h, a pH of 9, a temperature of 25° C., and a volume of 50 mL. Establishing the maximum loading capacities provided by the carriers and characterizing equilibrium aspects depend on the starting level of CPN, which is an issue that should be explored throughout the evaluation of any inspected loading behaviors of the carrier. The measured quantities of CPN loaded into the SNRs were higher when the studies were conducted using elevated concentrations of CPN, as shown in FIG. 8C.

The increased concentration of CPN ions within particular volumes results in an increment in the CPN mobility properties as well as its diffusion and the driving forces gained by its ions. This results in a collision alongside chemical interactions with the binding sites across the exteriors of SNRs, thereby enhancing the efficiency of the loading activities. The augmentation in the amount of entrapped CPN with respect to the starting level was detected up to 230 mg/L. The experiments conducted with levels of CPN higher than the aforementioned thresholds yielded neglected or nearly constant loading quantities, indicating the equilibrium/saturation phases of the utilized vehicles. Thus, the SNRs nanoparticles achieve an actual maximum CPN loading qualities of 288 mg/g, as shown in FIG. 8C.

Example 12: Intra-Particle Diffusion Properties

Figure 8D:
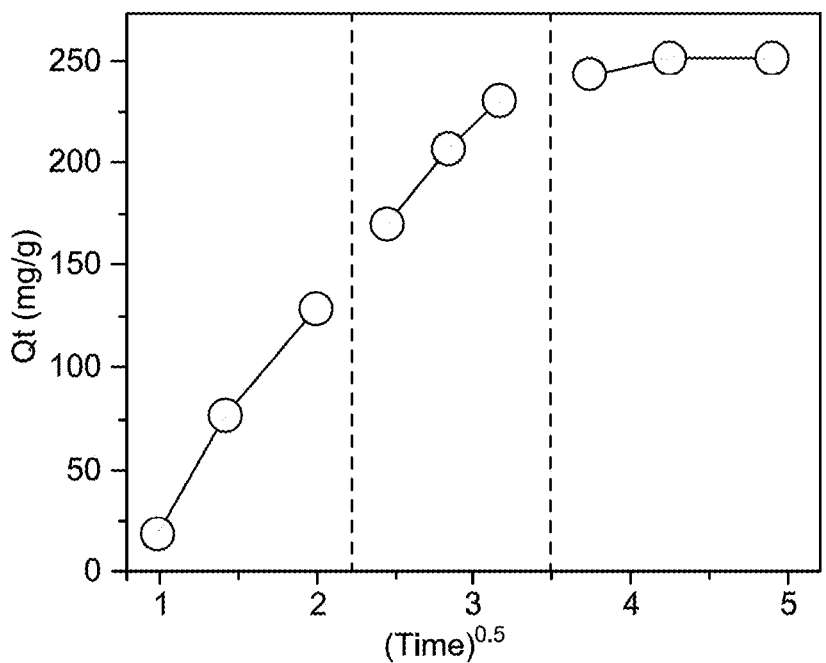
FIG. 8D is an intra-particle diffusion curve associated with CPN loading into the SNRs, according to certain embodiments.

The present disclosure evaluated the intra-particle diffusion patterns associated with CPN loading into the SNRs in order to identify aspects that affect the loading processes, as shown in FIG. 8D. The existing curves possess segmentation characteristics, along with multiple lines that may not intersect with the starting points. The findings from the analysis of CPN loading behaviors indicate that the entrapping activities of CPN into the SNRs are controlled by multiple types of regulatory mechanisms instead of only by the intra-particle diffusion reaction. The obtained graphs of the vehicles that were examined reveal that three successive phases of regulation were implemented during the course of the loading processes. These phases include exterior retention, intra-particle diffusion and/or layered retention, and saturating phases. The earliest discernible portion of the graph shown in FIG. 8D illustrates the phase of exterior adsorption that occurs across the outermost layers of the surfaces of the SNRs.

The presence of functioning binding or receptor sites over the SNRs interfaces has an impact on the loading phase. The second phase of the graph shown in FIG. 8D corresponds to the intra-particle diffusion process. Within this step, the CPN ions migrate and diffuse through the interior porosity inside the SNRs nanomaterials and bond to their interior receptor sites without any influence on the exterior loading sites. The third portion of the graph shown in FIG. 8D, designated as the equilibration and saturating phases, reveal a negligible or absent enhancement in the CPN loading qualities of SNRs. The equilibration phase has been effectively completed owing to the complete occupancy of all accessible sites and the development of thickly loaded layers of CPN over the outer surface of the SNRs via molecular associations and inter-ionic attractions.

Example 13: Kinetic Modeling

Figure 8E:
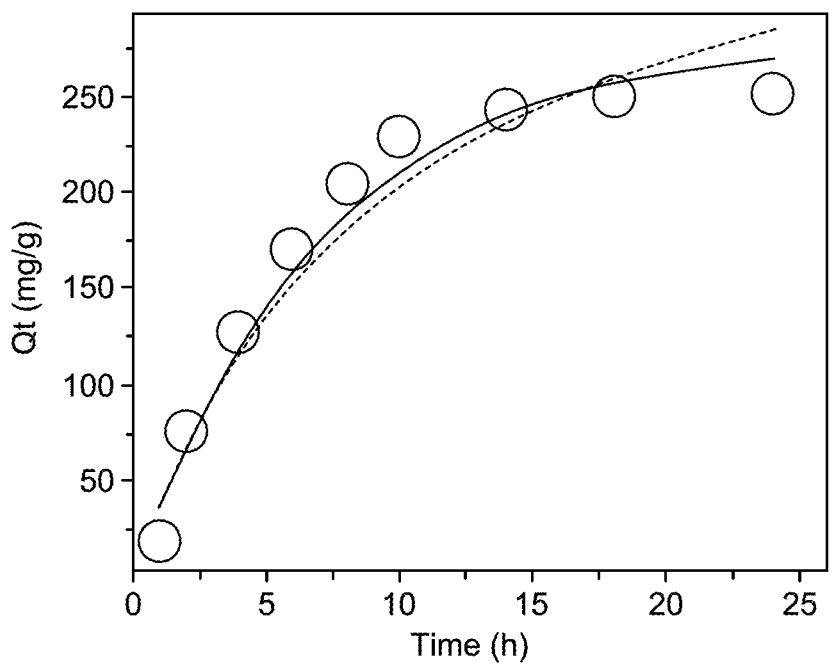
FIG. 8E is a graph depicting kinetic modeling of the loading operations of CPN into the SNRs, according to certain embodiments.

Theoretical factors and assumptions of the pseudo-first order (PFO) theory, as listed in Eq. 4, and pseudo-second order (PSO) theory, as listed in Eq. 5, were implemented to analyze the kinetic simulations of the loading operations of CPN into SNRs, as shown in FIG. 8E. The alignment levels were determined using nonlinear fit, which included computing the correlation coefficient ($R^2$) and chi-square ($X^2$) results.

$$Q_t = Q_e(1 - e^{-k_1 t}) \quad (4)$$

$$Q_t = \frac{Q_e^2 k_2 t}{1 + Q_e k_2 t} \quad (5)$$

The loading activities of CPN through the SNRs follow the kinetic aspects corresponding to the PFO theory, which are demonstrated by calculating the $R^2$ and $X^2$ parameters. The concordance of the analytical findings (251.7 mg/g) with the predicted levels of $Q_e$ (266.4 mg/g) supports the consistency of the findings with the proposed kinetic aspects of PFO. This kinetic tendency correlates to physical loading processes, such as Van der Waals forces and electrostatic attraction. Further, the modes of encapsulation correlate better with the PFO concepts versus the PSO hypotheses. The CPN loading interactions across the SNRs show a correlation with the displayed formula of the PSO concept.

Therefore, other chemisorption processes, such as electron exchanges, hydrogen bonding, and chemical complexes, may play a secondary role or show a minor effect throughout the loading processes of CPN. The intricate interaction of physical and chemical processes may be attained through the generation of a layer of chemically bonded CPN, which may then be used as a base for introducing further layers of loaded CPN through physical processes.

Example 14: Classic Isotherm Modeling

Figure 8F:
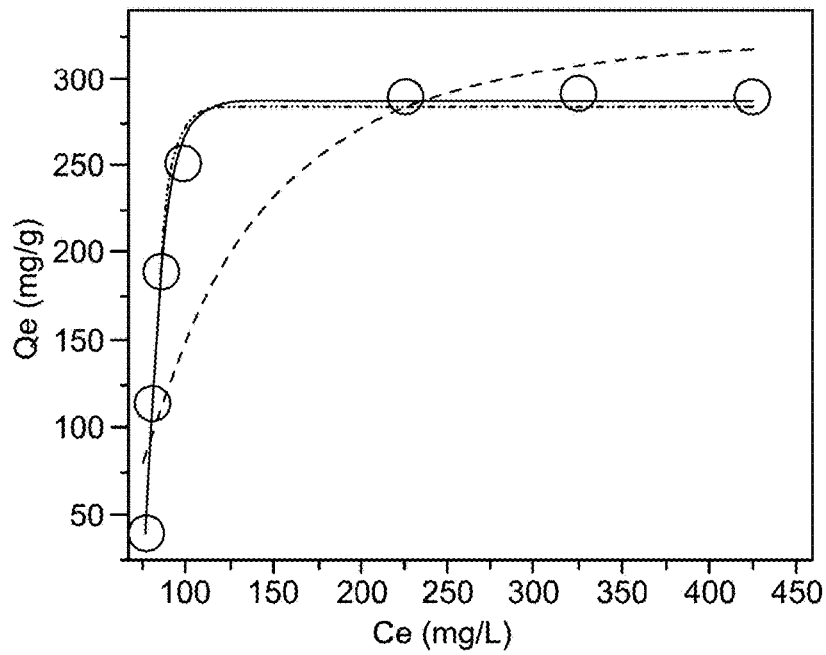
FIG. 8F is a graph depicting classic isotherm modeling of the SNRs, according to certain embodiments.

The equilibrium characteristics of the CPN entrapping mechanistic activities across SNRs, as shown in FIG. 8F, has been assessed using three common isotherm approaches, including the Langmuir approach (Eq. 6), the Freundlich approach (Eq. 7), and Dubinin-Radushkevich (D-R) approach (Eq. 8). The $R^2$ and $X^2$ indices have been determined by nonlinear matching to assess the level of fits.

$$Q_e = Q\max\, bCe/(1 + bCe) \quad (6)$$

$$Q_e = K_f C_e^{1/n} \quad (7)$$

$$Q_e = Q_m e^{-\beta \varepsilon^2} \quad (8)$$

The levels of $R^2$ and $X^2$ indicate a better correlation with the isotherm principle of the Langmuir theory, suggesting monolayer and homogeneous loading activities of CPN by SNRs. Further, the equilibration parameter (RL) estimated values based on the Langmuir simulation are less than one, indicating that CPN possesses favorable trapping properties into SNRs. Depending on Langmuir's isotherm evaluation, the predicted maximum loading capabilities (Qmax) of CPN into the SNRs was 283.7 mg/g. The D-R model does a good job of demonstrating how the energy levels change in the SNRs during CPN loading operations, no matter how homogeneous or heterogeneous the interfaces are. The Gaussian energy (E) provided by the D-R theory has a function in establishing the types of reactions involved in the uptake of CPN, irrespective of whether those processes are chemical or physical.

Intensive physical reactions occur when the energy levels are below 8 KJ/mol, while weak chemical or intricate physical or chemical activities exist whenever energy levels range from 8 to 16 KJ/mol. Elevated levels that exceed 16 KJ/mol indicate the existence of powerful chemical pathways. The measured energy levels during the CNP loading processes match the range of the physical reactions and are close to the suggested limits of complex physical and chemical pathways. Therefore, the loading of CPN loading may have been impacted by poor chemical reactions.

Example 15: Advanced Equilibrium Studies

Figure 8G:
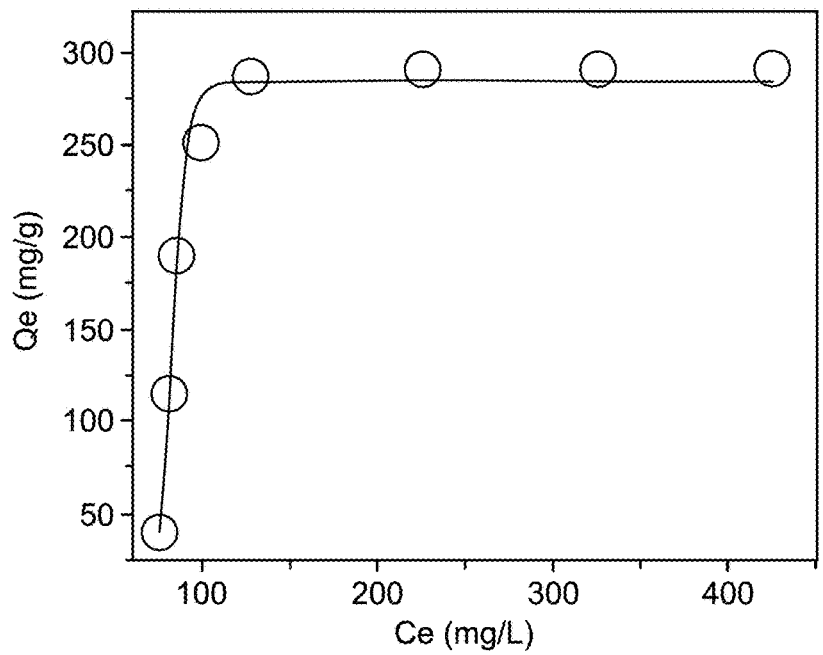
FIG. 8G is a graph depicting advanced isotherm modeling of the SNRs, according to certain embodiments.

Modern isotherm models derived from statistical physics were investigated to determine the process by which CPN may be loaded into SNRs. The monolayer model of a single energy site (Eq. 9) was selected to represent and illustrate the CPN loading results, as shown in FIG. 8G. The model exhibited the greatest $R^2$ value and the smallest root mean square error (RMSE).

$$Q = nNo = \frac{nN_M}{1 + \left(\frac{C_{1/2}}{Ce}\right)^n} = \frac{Q_0}{1 + \left(\frac{C_{1/2}}{Ce}\right)^n} \quad (9)$$

To elucidate general loading processes, the computational variables of the model were determined and evaluated. The energetic factors (loading energy (E)) alongside steric variables (density of loading receptor ($N_M$)), the number of CNP ions trapped into a single receptor (n), and saturating loading capacity ($Q_{sat}$) have been provided. The density of the contributing receptors ($N_M$) encountered an existence of effective receptors of 14.5 mg/g, illustrating the elevated loading properties of the SNRs at saturation situations ($Q_{sat}$=282.75 mg/g). In addition, the functioning procedure led to an increase in the trapping performance of each reactant receptor or binding site. Specifically, each receptor across the structure of the SNRs may accommodate up to 20 molecules of CPN. Furthermore, the detection of the value of n>1 implies the existence of multi-molecular pathways involved in the trapping of CPN across SNRs, as well as the vertical alignments of the CPN ions that have already been loaded.

The loading energy (E) was established by applying Eq. 10 to recognize the mechanisms (chemical or physical) that impact the trapping of CPN into SNRs.

$$\Delta E = -RT\ln\left(\frac{s}{C1/2}\right) \quad (10)$$

The uptake energies for SNRs, though the loading of CPN, were determined to be around −4.3 KJ/mol. The prior values reveal that the incorporation of CPN into the SNRs may be accomplished via physical mechanistic pathways such as dipole bond forces (E=2 KJ/mol to 29 KJ/mol), Van der Waals forces (E=4 KJ/mol to 10 KJ/mol), electrostatic attraction (E=2 KJ/mol to 50 KJ/mol), and hydrogen bonding (E=30 KJ/mol).

Example 16: In-Vitro Release Profiles

Figure 8H:
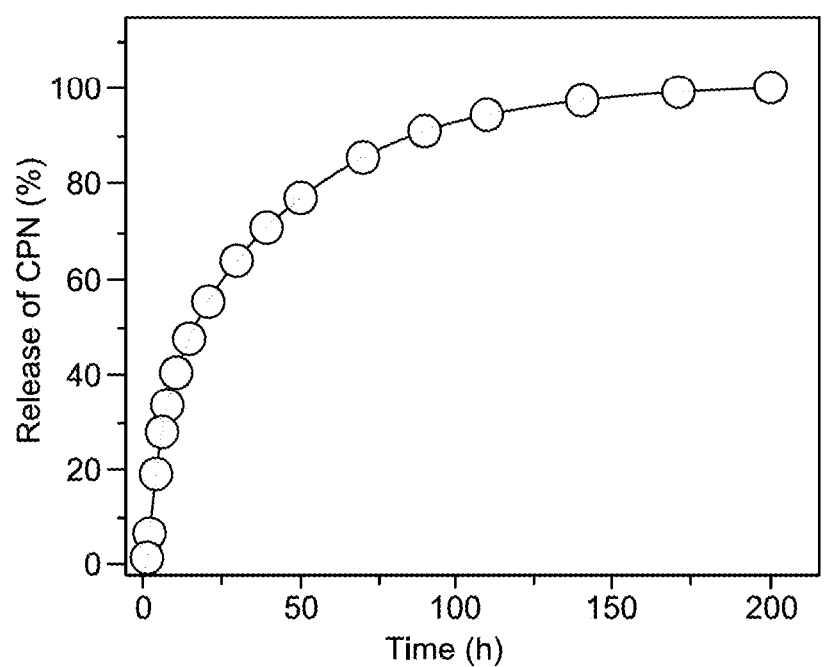
FIG. 8H is a graph depicting the release profile of CPN from the SNRs at a pH of 5.5, according to certain embodiments.
Figure 8I:
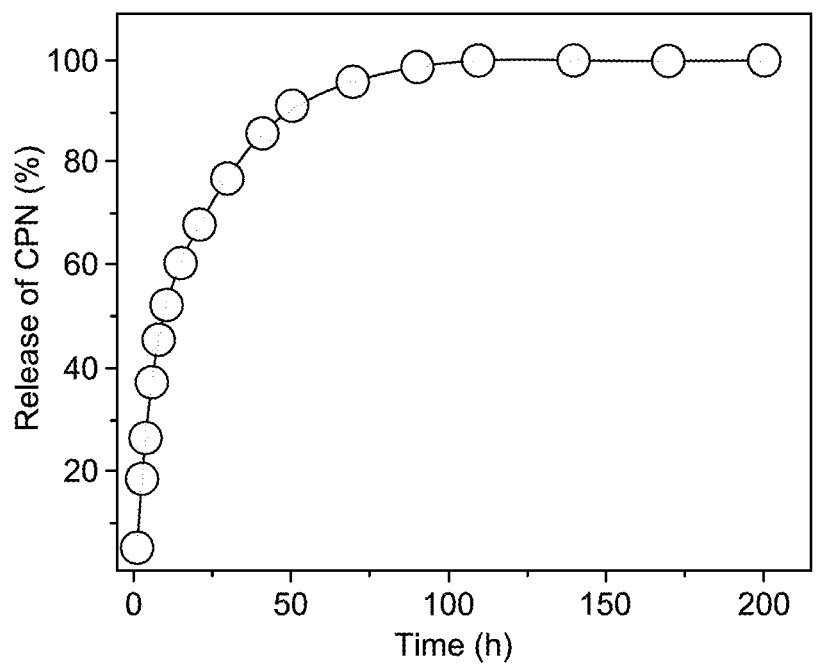
FIG. 8I is a graph depicting the release profile of CPN from the SNRs at a pH of 7.4, according to certain embodiments.

The assessment of the CPN-releasing behaviors out of the SNRs was conducted employing the determined quantities of CPN molecules that migrated through two specific buffers, phosphate (pH 7.4) and acetate (pH 5.5), that were utilized to replicate the conditions and settings of the malignant cells, as shown in FIG. 8H and FIG. 8I, respectively. The CPN was released at a certain percentage of both SNRs through the two tested buffering solutions. The observed rates showed variances, with a rise in the release time frame. The SNRs demonstrate elevated rates of CPN release during the first release period, which has been linked to fluctuations in the amount of CPN liberated. The rates of CPN migration realized a drop after a particular duration of release.

There were no noticeable differences in releasing characteristics, indicating a consistent response by the end of the assessment. The fast migration of CPN throughout the initial releasing phases may be caused by the immediate desorption of CPN through the weakly and physically bonded ions via the exterior receptors throughout SNRs. Once the weakly bonded and surface-loaded CPN had been fully liberated from the structures of SNRs, the release behavior was mostly affected by the migration of the strongly chemically adsorbed ions and those forming types of complexes. The CPN ions that were encapsulated within the internal pores of the SNRs framework also had an effect on the observed diffusion speeds. In addition, as compared to the standard conditions (pH 7.4 using a phosphate buffer), the observed release activity of CPN from the SNRs was enhanced in the acidic setting (pH 5.5 using an acetate buffer). The enhanced CPN-releasing characteristics at pH 5.5 compared to pH 7.4 were due to the expected destructive effect of the low pH state on the framework of SNRs, which enhanced its ability to release CPN quickly. The CPN-releasing behaviors of the SNRs in phosphate or acetate buffers were tracked for roughly 200 hours; however, the complete release levels were not identified. Following a duration of 110 h and 200 h, the loaded quantity of CPN was liberated at pH 5.5 and pH 7.4, as shown in FIG. 8H and FIG. 8I, respectively.

In certain situations, it may be beneficial to have sustained and extended contact between the drug ions and the malignant cells. Consequently, specialists have proposed delivery mechanisms that possess progressive and regulated diffusion aspects. Specific situations where it may be beneficial to provide therapeutic doses over brief periods support the implementation of rapid and abrupt delivery systems. Therefore, synthetic SNRs have the potential to be effective carriers for the regulated encapsulation and diffusion of CPN.

Example 17: Cytotoxicity and Anticancer Properties

The antitumor activities of free CPN were compared to those of SRNs and CPN-loaded SNRs against human cervical epithelial malignancies (HeLa). The free CPN drug displayed a cytotoxic impact on the HeLa cancerous cells, especially at the highest applied dosage of about 1 μg/mL, and this effect increased gradually with increasing the incubation duration (cell viability=18.6% at 24 h, 9.9% at 48 h, and 6.6% at 72 h). Regarding the anticancer activities of SRNs as free particles, they also exhibit marked cytotoxicity effects on the cancerous cells, reflecting their effect as either delivery for chemotherapy or anticancer agents. The determined cell viability using the SNRs (1 μg/mL) are 45.8% (24 h), 31.7% (48 h), and 22.4% (72 h). The anticancer activities of the CPN drug were enhanced after the encapsulation of its molecules into SNRs. The cytotoxic effects on the cancerous cells increased at a rate of the CPN-loaded SNRs to be 9.3%, 3.2%, and 0.87% after the incubation periods of 24 h, 48 h, and 72 h, respectively. Therefore, the results in terms of loading, release, and cytotoxic properties recommend the application of the SNRs effectively as an anticancer agent and carrier for CPN for effective chemotherapy treatment of HeLa cancerous cells.

Aspects of the present disclosure provide aluminum silicate nanorods (SNRs) and a method of preparation thereof and the use of the aluminum silicate nanorods for treating cancers. The SNRs were developed from natural glauconite minerals using sono-chemical scrolling techniques. The developed SNRs structure was assessed as a biocompatible nanomaterial with enhanced physiochemical and biological properties as an anticancer agent, as well as advanced delivery systems for the cisplatin drug (CPN) during the treatment of human cervical epithelial malignancies (HeLa). The structure is developed to mitigate commonly reported drawbacks of CPN as an anticancer therapy, which include toxicity, nephrotoxicity, and a plurality of health side effects. By morphologically modifying naturally occurring glauconite minerals in high geological reserves, the developed structure, when compared to commonly applied carriers and anticancer agents, exhibits good biocompatible properties, anticancer activity, and value as a low-cost product. As a nano-delivery system, the SNRs may reduce the commonly reported side effects of the CPN by controlling the release of the CPN over long periods of time, which have a stronger inhibitory effect on cancerous cells.

Numerous modifications and variations of the present disclosure are possible in light of the above teachings. It is therefore to be understood that within the scope of the appended claims, the disclosure may be practiced otherwise than as specifically described herein.

The invention claimed is:
1. A method of cytotoxically treating cancer with a nanocomposite, including:
   contacting aluminum silicate nanorods at a concentration of 0.5 to 2 μg/mL with a cancerous sample,
   wherein the aluminum silicate nanorods comprise aluminum, iron, magnesium, oxygen, and potassium,
   wherein the aluminum silicate nanorods have a longest dimension of 100 to 5500 nm and a diameter of 20 to 250 nm,
   wherein the aluminum silicate nanorods are porous with a pore size of 1 to 12 nm,
   wherein the aluminum silicate nanorods include cisplatin in an amount of 20 to 300 mg/g, wherein at least a portion of the cisplatin is encapsulated by the aluminum silicate nanorods,
   wherein the cancerous sample has a reduced cell viability after the contacting.
2. The method of claim 1, wherein the aluminum silicate nanorods are rolled nanosheets of an exfoliated glauconite.
3. The method of claim 1, wherein the aluminum silicate nanorods are made by a process including:
   grinding a glauconite;
   dispersing and stirring the ground glauconite in a polar solvent for 70 to 75 h,
   wherein the dispersing and stirring breaks intermolecular bonds in the glauconite,
   washing the dispersed glauconite 4 to 6 times for 10 to 30 minutes each time with methanol to form a methoxy glauconite;
   immersing and stirring the methoxy glauconite in an aqueous cetyltrimethylammonium bromide solution for 45 to 50 h at 800 to 1200 rpm to form exfoliated methoxy glauconite layers,
   sonicating the exfoliated methoxy glauconite layers at a power supply of 230 to 250 W for 90 to 100 h to form a product,
   wherein the sonicating rolls the exfoliated methoxy glauconite layers into the product, filtering, washing with deionized water, and drying the product at 50 to 70 degrees Celsius (° C.) to form the aluminum silicate nanorods.

4. The method of claim 3, wherein the polar solvent is a 5:95 to 25:75 volume to volume (v/v) ratio mixture of water to dimethyl sulfoxide.

5. The method of claim 1, wherein the cisplatin is present on an outer surface of the aluminum silicate nanorods.

6. The method of claim 1, wherein the cisplatin interacts with the pores and the outer surface of the aluminum silicate nanorods through hydrogen bonding and van der Waals forces.

7. The method of claim 1, wherein the aluminum silicate nanoroads are formed by mixing the nanorods with a cisplatin solution at a pH of 2 to 10.

8. The method of claim 1, wherein the aluminum silicate nanorods are formed by mixing the nanorods with cisplatin for 0.5 to 25 h.

9. The method of claim 1, wherein the aluminum silicate nanorods have a saturation loading capacity of 200-350 milligram of cisplatin per gram of nanorod (mg/g).

10. The method of claim 1, wherein the aluminum silicate nanorods have a density of loading receptor value of 12 to 17 mg/g.

11. The method of claim 1, wherein the aluminum silicate nanorods have binding site and each binding site accommodates 15 to 25 molecules of cisplatin.

12. The method of claim 1, wherein the aluminum silicate nanorods release cisplatin for 190 to 210 h at a pH of 5.4 to 5.6.

13. The method of claim 1, wherein the aluminum silicate nanorods release cisplatin for 100 to 120 h in a solution at a pH of 7.3 to 7.5.

14. The method of claim 1, wherein the aluminum silicate nanorods have a surface area of 120 to 130 $m^2/g$.

15. The method of claim 1, wherein the aluminum silicate nanorods have an average pore diameter of 3 to 5 nm.

16. The method of claim 1, wherein the aluminum silicate nanorods have an uptake energy for the cisplatin of −6 to −2 KJ/mol.

17. The method of claim 1, wherein the cell viability of the cancerous sample is 2 to 5% after 48 h of contacting.

18. The method of claim 1, wherein the cell viability of the cancerous sample is 0.5 to 1.0% after 72 h of contacting.

* * * * *